(12) United States Patent
Nakanishi et al.

(10) Patent No.: US 8,872,114 B2
(45) Date of Patent: Oct. 28, 2014

(54) INSPECTION APPARATUS AND INSPECTION METHOD

(75) Inventors: Hidetoshi Nakanishi, Kyoto (JP); Masayoshi Tonouchi, Suita (JP); Iwao Kawayama, Suita (JP)

(73) Assignees: Dainippon Screen Mfg. Co., Ltd., Kyoto (JP); Osaka University, Osaka (JP)

( * ) Notice: Subject to any disclaimer, the term of this patent is extended or adjusted under 35 U.S.C. 154(b) by 175 days.

(21) Appl. No.: 13/494,754

(22) Filed: Jun. 12, 2012

(65) Prior Publication Data

US 2013/0015368 A1     Jan. 17, 2013

(30) Foreign Application Priority Data

Jul. 14, 2011    (JP) ................................. 2011-155665
Sep. 13, 2011    (JP) ................................. 2011-199309

(51) Int. Cl.
| | | |
|---|---|---|
| G01N 21/35 | (2014.01) | |
| G01N 21/95 | (2006.01) | |
| G01N 21/956 | (2006.01) | |
| G01R 31/26 | (2014.01) | |

(52) U.S. Cl.
CPC ........ G01N 21/3586 (2013.01); G01N 21/9501 (2013.01); G01N 21/956 (2013.01); G01N 21/3563 (2013.01); G01R 31/2605 (2013.01)
USPC .................. 250/358.1; 250/341.1; 250/341.4; 250/338.1; 250/458.1; 250/459.1; 324/754.23

(58) Field of Classification Search
CPC .......... G01N 21/3586; G01N 21/3581; G01N 21/9501; G01N 21/956; G01N 21/7703; G01R 31/2635; G01R 31/2605; G01R 31/308; G01R 31/2637; G01R 31/405; H01L 22/10; H01L 22/14
USPC .......... 250/458.1, 459.1, 338.1, 358.1, 341.1, 250/341.4; 324/754.23
See application file for complete search history.

(56) References Cited

U.S. PATENT DOCUMENTS

| | | | |
|---|---|---|---|
| 7,852,102 B2 * | 12/2010 | Kitagawa et al. ........ | 324/762.01 |
| 8,129,683 B2 | 3/2012 | Itsuji et al. | |
| 2003/0067312 A1 | 4/2003 | Pfaff et al. | |

(Continued)

FOREIGN PATENT DOCUMENTS

| | | |
|---|---|---|
| CN | 101561475 A | 10/2009 |
| CN | 101581756 A | 11/2009 |

(Continued)

OTHER PUBLICATIONS

European Search Report issued in European Patent Application No. 12170803.6 dated Oct. 31, 2012.

*Primary Examiner* — David Porta
*Assistant Examiner* — Adam J Fifth
(74) *Attorney, Agent, or Firm* — McDermott Will & Emery LLP

(57) ABSTRACT

A technology of inspecting a photoexcited carrier generation area of a photo device in a non-contact manner is provided. An inspection apparatus inspects a photovoltaic cell panel in which the photo device is formed. The inspection apparatus includes an irradiation part that irradiates the photovoltaic cell panel with pulsed light from a light receiving surface side and a detecting part (detector) that detects electric field intensity of a terahertz wave pulse, which is generated according to the irradiation of the pulsed light.

17 Claims, 18 Drawing Sheets

(56) References Cited

U.S. PATENT DOCUMENTS

| | | |
|---|---|---|
| 2006/0006886 A1 | 1/2006 | Yamashita et al. |
| 2007/0218376 A1 | 9/2007 | Ouchi |
| 2008/0186239 A1 | 8/2008 | Itsuji |
| 2010/0201349 A1 | 8/2010 | Taira et al. |
| 2010/0219327 A1 | 9/2010 | Arbore et al. |
| 2011/0216312 A1 | 9/2011 | Matsumoto et al. |

FOREIGN PATENT DOCUMENTS

| | | |
|---|---|---|
| EP | 1441233 A1 | 7/2004 |
| JP | 05226431 A | 9/1993 |
| JP | 2009-175127 A | 8/2009 |
| JP | 2010-182969 | 8/2010 |
| WO | WO-2010/024324 A1 | 3/2010 |

\* cited by examiner

F I G. 1
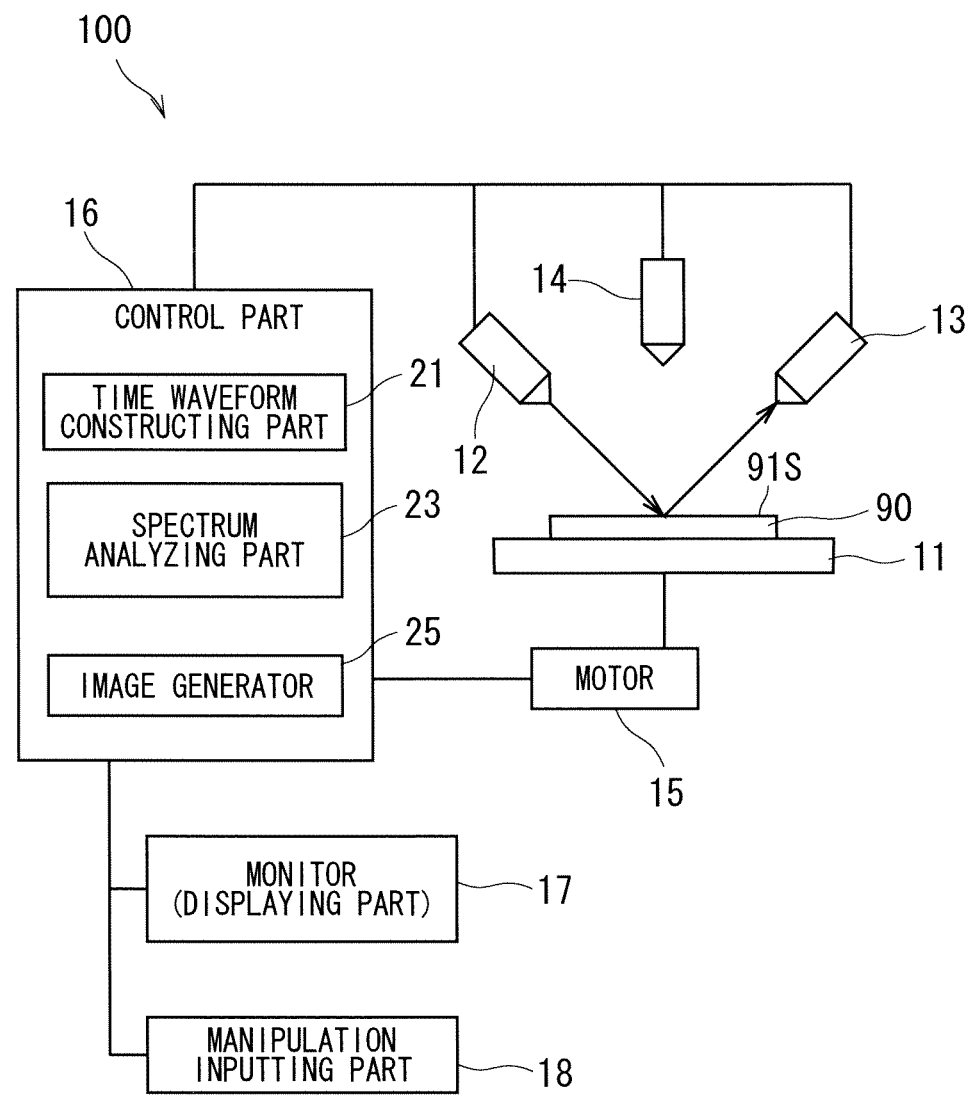

FIG. 7
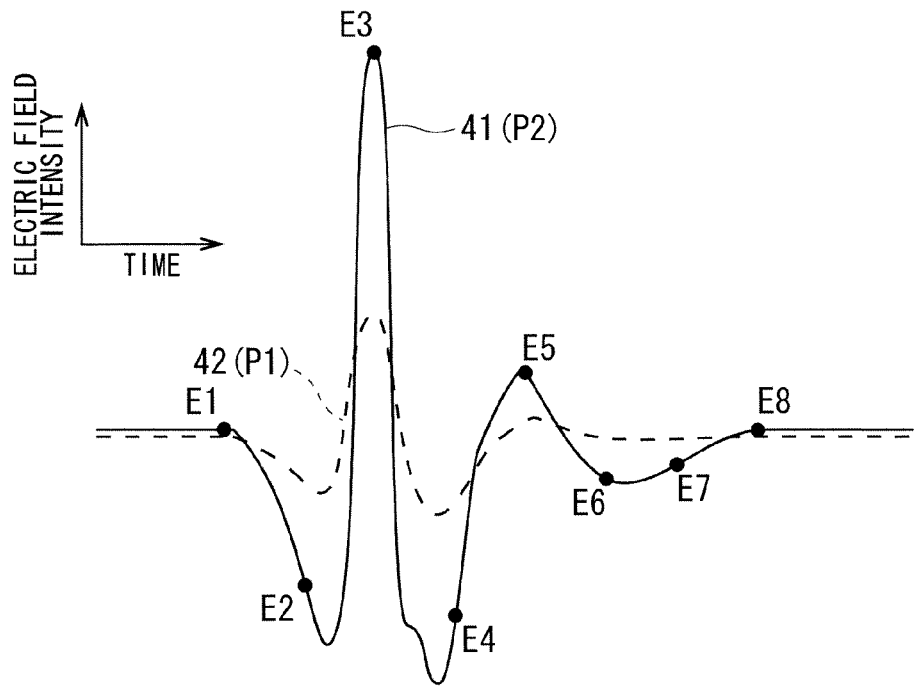
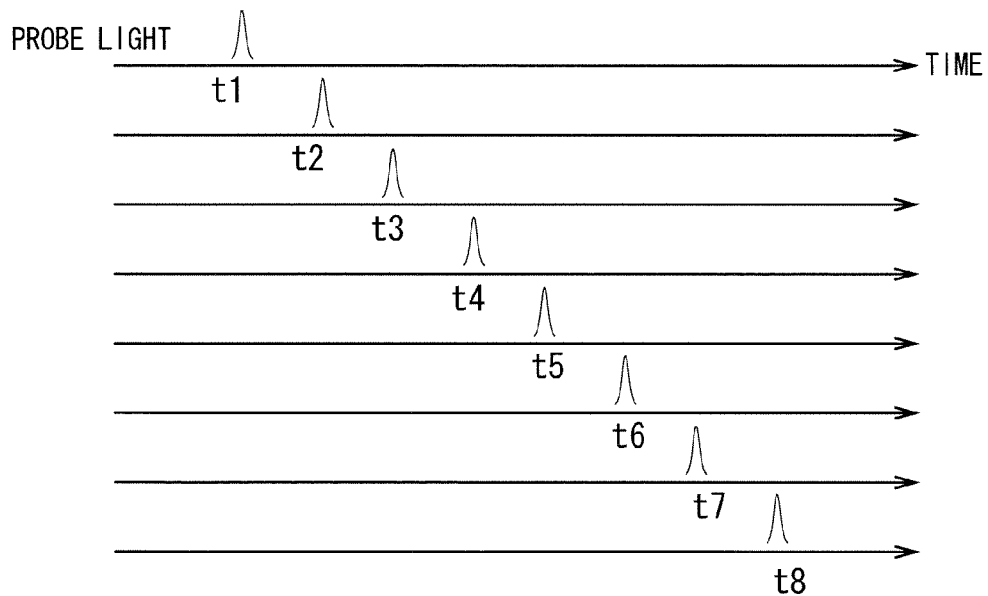

F I G . 8
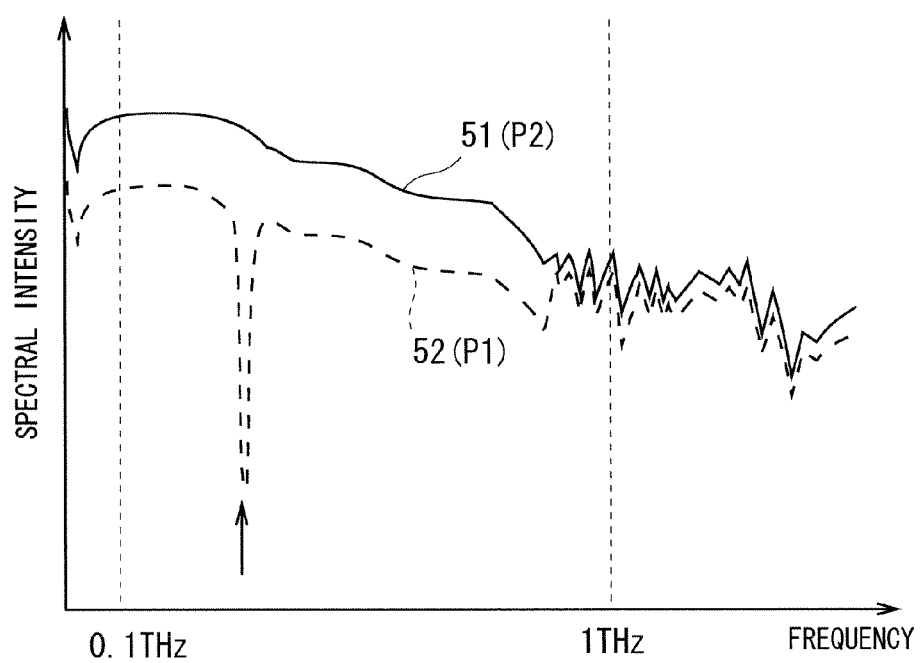

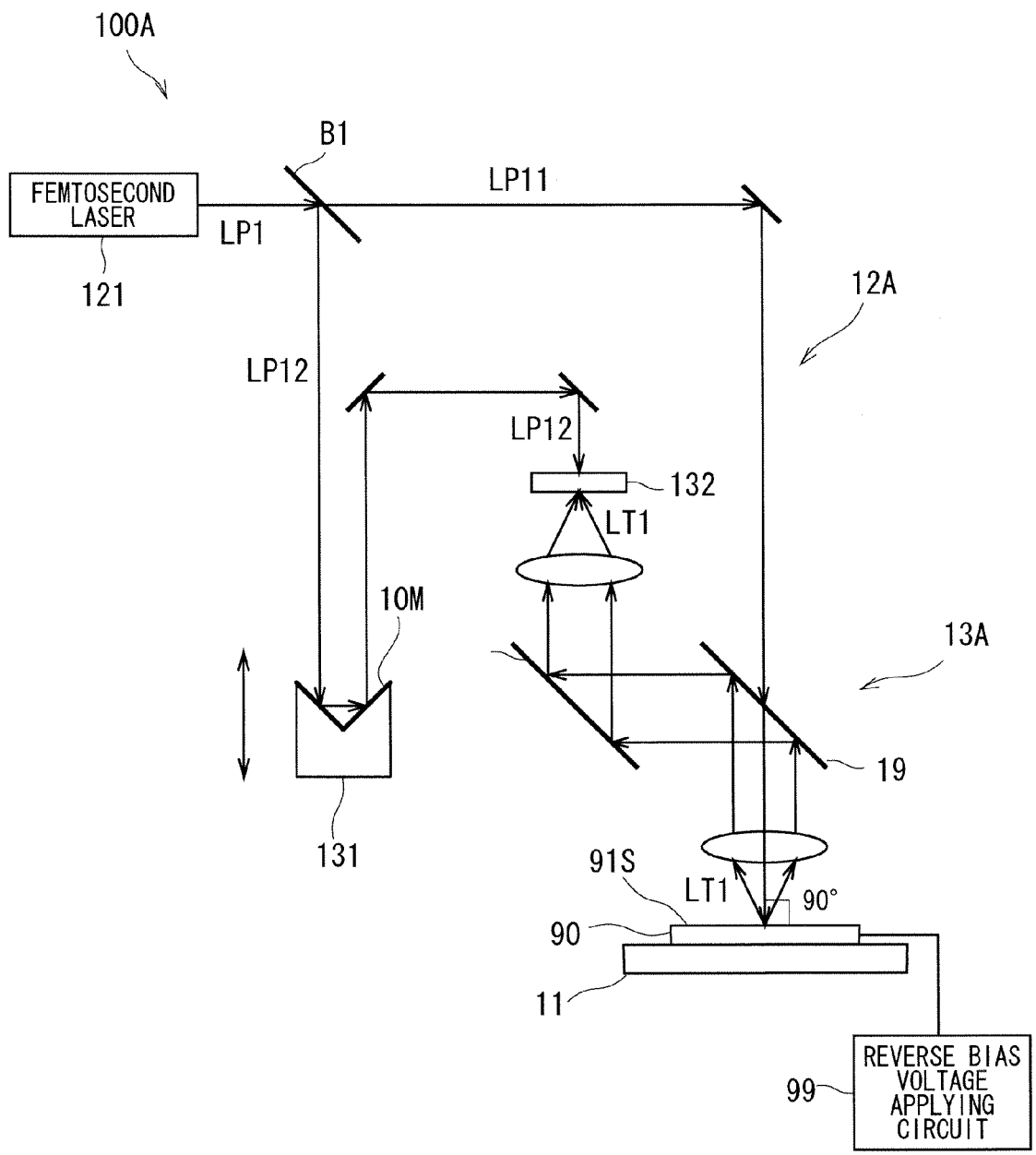
F I G . 1 1

F I G . 1 3
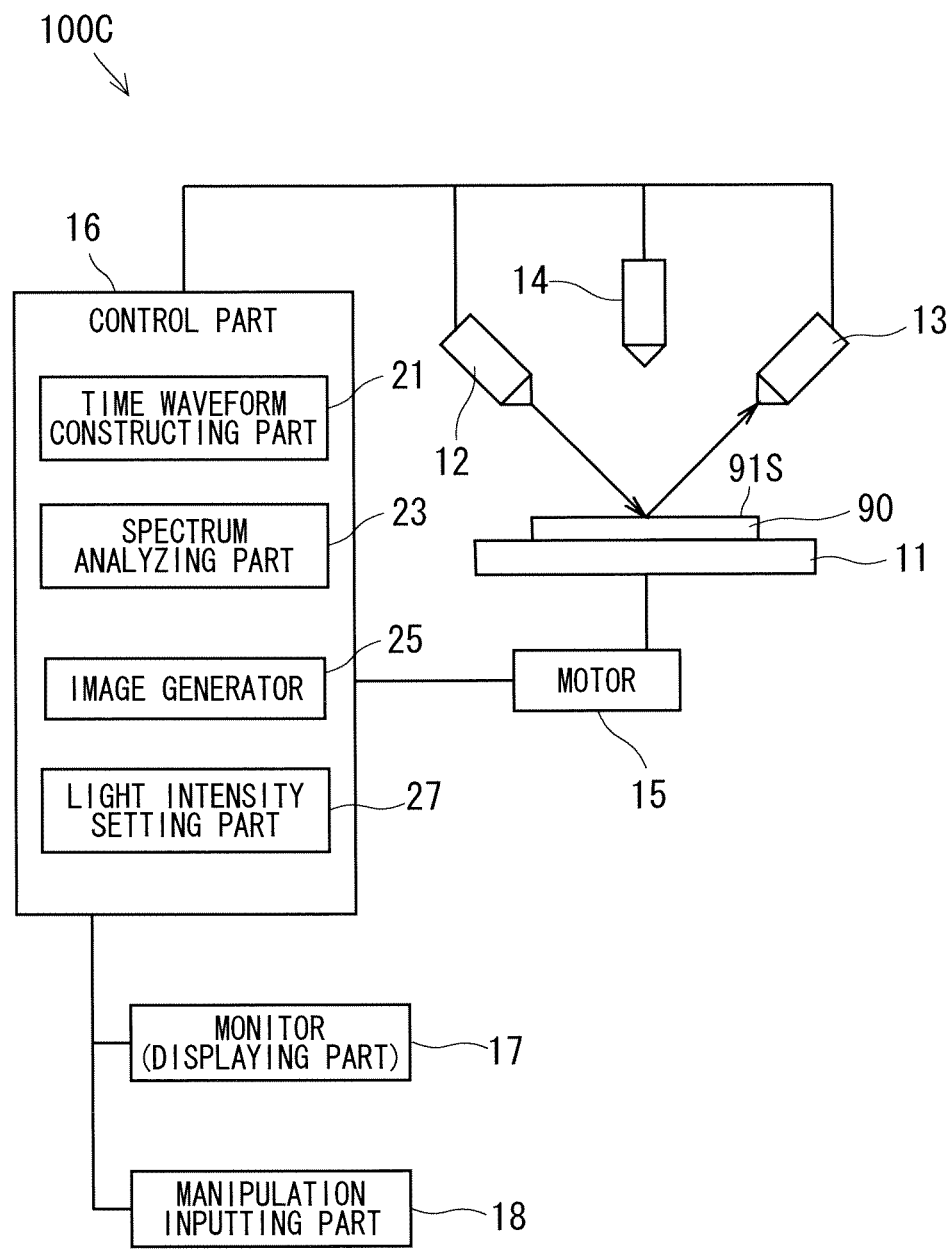

F I G . 1 4
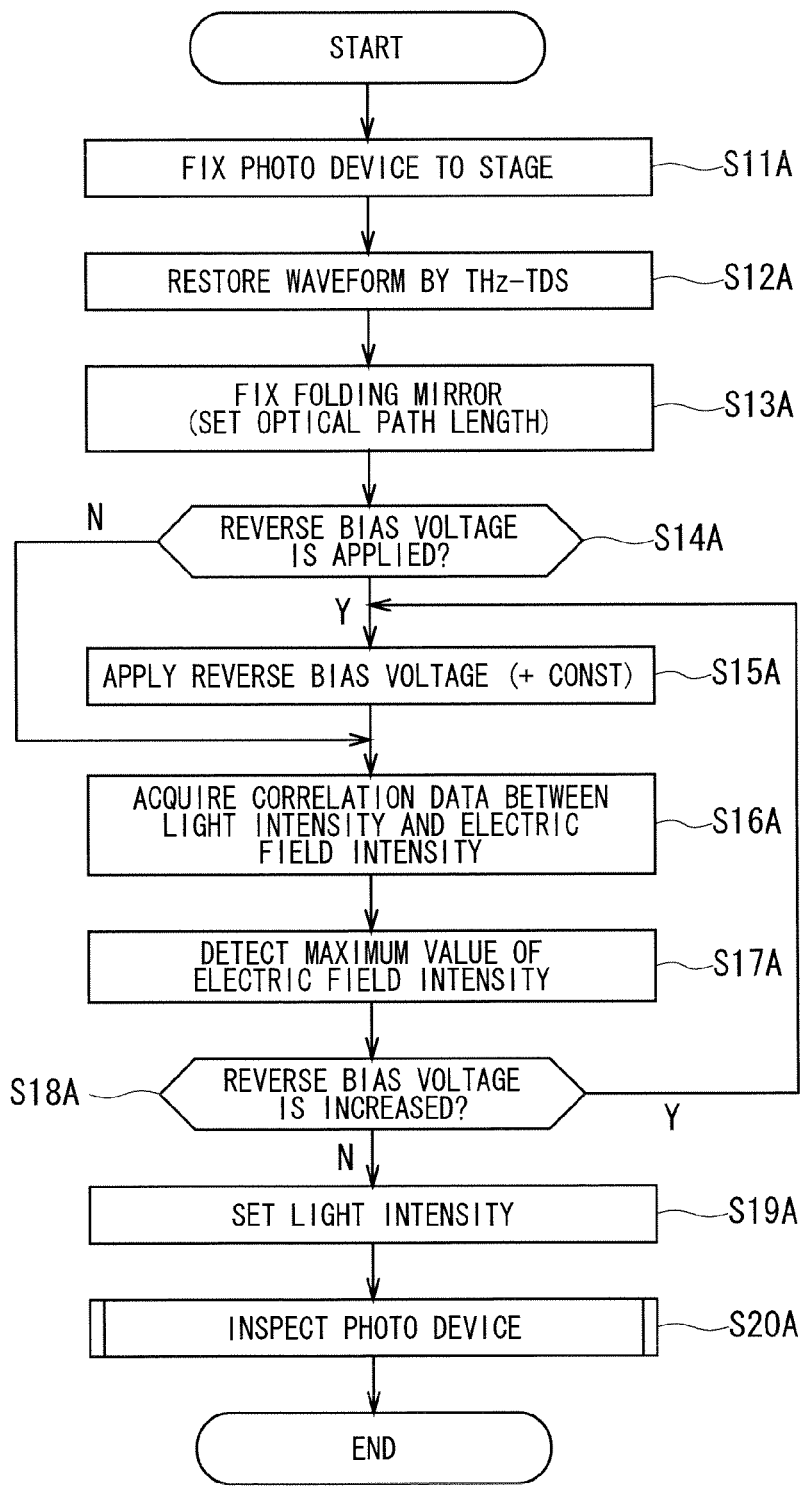

| CD1 | REVERSE BIAS VOLTAGE (V) | | | | | | |
|---|---|---|---|---|---|---|---|
| LIGHT INTENSITY (mW) | | 0 | 1 | 2 | 4 | 6 | 8 | 10 |
| | 0 | 0.5 | 0.5 | 0.5 | 0.5 | 0.5 | 0.5 | 0.5 |
| | 0.5 | 0.5 | 0.5 | 0.5 | 0.5 | 0.5 | 0.5 | 0.5 |
| | 1 | 0.5 | 0.5 | 0.5 | 0.5 | 0.6 | 0.6 | 0.7 |
| | 3 | 0.5 | 0.5 | 0.5 | 0.5 | 0.6 | 0.7 | 0.8 |
| | 5 | 0.5 | 0.5 | 0.6 | 0.9 | 1.2 | 1.3 | 1.5 |
| | 8 | 0.5 | 0.7 | 0.9 | 1.4 | 1.9 | 2.1 | 2.5 |
| | 10 | 0.5 | 0.7 | 1.2 | 1.8 | 2.4 | 2.8 | 3.2 |
| | 15 | 0.5 | 1.0 | 1.5 | 2.7 | 3.4 | 4.3 | 5.0 |
| | 20 | 0.5 | 1.0 | 1.9 | 3.2 | 4.5 | 5.5 | 6.4 |
| | 30 | 0.5 | 0.5 | 1.7 | 3.9 | 5.6 | 7.2 | 8.7 |
| | 40 | 0.5 | 0.5 | 1.1 | 4.0 | 6.2 | 8.0 | 9.8 |
| | 50 | 0.5 | 0.5 | 0.6 | 3.7 | 6.1 | 8.3 | 10.3 |
| | 60 | 0.5 | 0.5 | 0.5 | 3.0 | 6.2 | 8.4 | 10.7 |
| | 70 | 0.5 | 0.5 | 0.5 | 1.4 | 5.5 | 8.3 | 10.5 |

| CD2 | \ REVERSE BIAS VOLTAGE (V) | | | | | | |
|---|---|---|---|---|---|---|---|
| LIGHT INTENSITY (mW) \ | 0 | 1 | 2 | 4 | 6 | 8 | 10 |
| 0 | 0.5 | 0.5 | 0.5 | 0.5 | 0.5 | 0.5 | 0.5 |
| 0.5 | 0.5 | 0.5 | 0.6 | 0.6 | 0.7 | 0.8 | 0.7 |
| 1 | 0.5 | 0.6 | 0.8 | 1.0 | 1.2 | 1.4 | 1.5 |
| 3 | 0.8 | 1.6 | 2.3 | 3.6 | 4.5 | 5.2 | 5.9 |
| 5 | 1.0 | 2.8 | 4.0 | 6.2 | 7.6 | 8.9 | 9.8 |
| 8 | 1.2 | 4.3 | 6.5 | 10.4 | 13.4 | 15.8 | 17.7 |
| 10 | (1.3) | 5.2 | 7.8 | 12.3 | 16.1 | 19.2 | 21.3 |
| 15 | 0.5 | 6.4 | 10.6 | 17.7 | 24.0 | 29.3 | 33.5 |
| 20 | 0.5 | (7.1) | 12.2 | 21.4 | 29.0 | 36.1 | 41.8 |
| 30 | 0.5 | 6.6 | (13.2) | 25.1 | 36.0 | 45.6 | 54.8 |
| 40 | 0.5 | 2.6 | 12.7 | (26.3) | 39.4 | 50.8 | 61.8 |
| 50 | 0.5 | 1.5 | 10.6 | 25.8 | 39.3 | 52.4 | 64.6 |
| 60 | 0.5 | 1.5 | 8.6 | 25.8 | (40.7) | (54.5) | (68.0) |
| 70 | 0.5 | 1.5 | 3.5 | 24.5 | 39.5 | 53.4 | (68.0) |

F I G . 1 7
CD3
| | 0 | 1 | 2 | 4 | 6 | 8 | 10 |
|---|---|---|---|---|---|---|---|
| 0 | 0.5 | 0.5 | 0.5 | 0.5 | 0.5 | 0.5 | 0.5 |
| 0.5 | 0.5 | 0.5 | 0.5 | 0.5 | 0.6 | 0.6 | 0.7 |
| 1 | 0.5 | 0.6 | 0.7 | 0.8 | 1.0 | 1.3 | 1.3 |
| 3 | 0.7 | 1.3 | 1.7 | 2.9 | 3.5 | 4.0 | 4.4 |
| 5 | (0.8) | 2.3 | 3.6 | 5.6 | 7.5 | 8.6 | 9.8 |
| 8 | (0.8) | 3.4 | 5.3 | 8.5 | 11.2 | 13.3 | 15.0 |
| 10 | 0.6 | 4.0 | 6.3 | 10.7 | 14.5 | 17.5 | 20.2 |
| 15 | 0.5 | (4.4) | 7.6 | 13.2 | 18.3 | 22.6 | 26.1 |
| 20 | 0.5 | 4.2 | (8.2) | 15.2 | 21.3 | 27.1 | 32.2 |
| 30 | 0.5 | 1.7 | 7.8 | (15.7) | (23.5) | 30.3 | 36.6 |
| 40 | 0.5 | 0.7 | 4.4 | 15.3 | (23.5) | (31.6) | (39.4) |
| 50 | 0.5 | 0.9 | 1.9 | 14.3 | 22.8 | 31.1 | (39.4) |
| 60 | 0.5 | 1.1 | 1.3 | 10.5 | 21.6 | 30.2 | 38.5 |
| 70 | 0.5 | 1.2 | 1.3 | 5.7 | 20.1 | 29.6 | 38.1 |
REVERSE BIAS VOLTAGE (V) *(column header)*
LIGHT INTENSITY (mW) *(row header)*
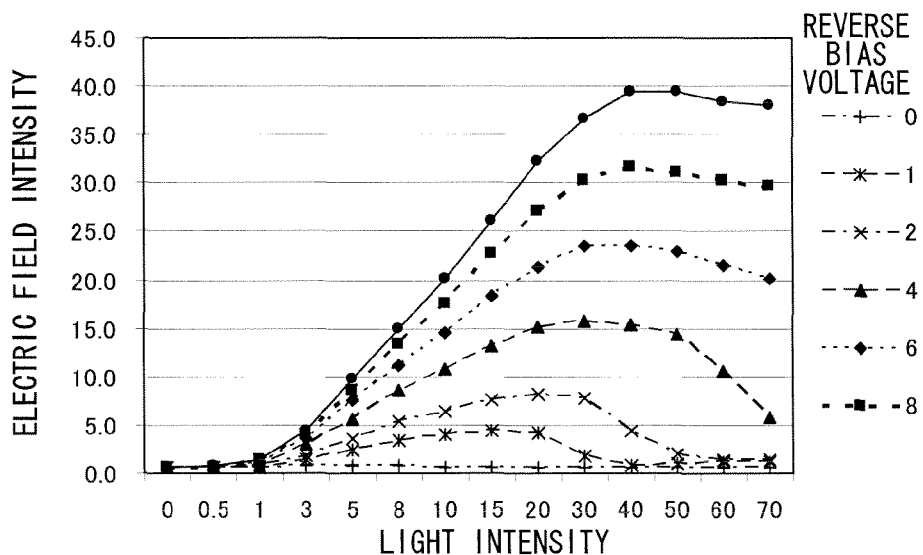

INSPECTION APPARATUS AND INSPECTION METHOD

BACKGROUND OF THE INVENTION

1. Field of the Invention

The present invention relates to a technology of inspecting a photo device.

2. Description of the Background Art

An inspection apparatus that measures an electric characteristic of the photovoltaic cell by utilizing what is called a four-terminal measurement method is used in a process of producing a photovoltaic cell that is of a kind of a photo device. Specifically, a current measuring probe pin and a voltage measuring probe pin are placed on collector electrodes provided in a light receiving surface and a rear surface of the photovoltaic cell. At this point, a voltage applied to the photovoltaic cell is changed while the photovoltaic cell is irradiated with pseudo-sunlight, thereby measuring a current-voltage relationship. Therefore, an I-V characteristic of the photovoltaic cell is measured (for example, see Japanese Patent Application Laid-Open No. 2010-182969).

SUMMARY OF THE INVENTION

In the conventional inspection apparatus for the photovoltaic cell, it is necessary to bring the current measuring probe pin or the voltage measuring probe pin into contact with the collector electrode. Therefore, there is a problem that the probe pin is worn down such that plating of the probe pin removes. Additionally, there is a risk of damaging a photovoltaic cell element during an inspection because the probe pin abuts on the photovoltaic cell.

The photo device such as the photovoltaic cell is constructed as an element that utilizes a free electron and a free hole, which are generated by irradiating a depletion layer of a pn junction with light. Electric field intensity or an electric field distribution in the depletion layer becomes an important parameter determining performance of the photo device. Accordingly, the performance of the photodiode can be evaluated by inspecting the depletion layer. However, there is hardly known a technology of inspecting the depletion layer of the photo device in a non-contact manner.

In addition to the depletion layer, various electric fields exist in the photo device. Specific examples of the electric field include an internal electric field generated by a crystal defect or a contact between a metal and a semiconductor and an external electric field generated by applying a reverse bias voltage. Although photoexcited carrier generation areas caused by the electric fields exist in the photo device, there is hardly known a technology of inspecting the areas in the non-contact manner. Diffusion information on a photoexcited carrier in the photoexcited carrier generation area is also a parameter that relates to the performance of the photo device. However, there is hardy known a technology of inspecting the diffusion information in the non-contact manner.

The present invention is directed to provide an inspection apparatus that inspects the photo device and an inspection method.

To solve the above problems, according to a first aspect, an inspection apparatus that inspects a photo device includes: an irradiation part that irradiates the photo device with pulsed light; and a detecting part that detects an electromagnetic wave pulse, which is generated by the photo device according to the pulsed light irradiation.

According to the inspection apparatus of the first aspect, the electromagnetic wave pulse is emitted to the outside according to the characteristic of the photoexcited carrier generation area by irradiating the photoexcited carrier generation area such as the depletion layer of the pn junction of the photo device with the pulsed light. A status such as a shape and a defect of the photoexcited carrier generation area and mobility of the photoexcited carrier can be inspected in the non-contact manner by detecting the electric field intensity of the electromagnetic wave pulse.

According to a second aspect, in the inspection apparatus of the first aspect, the detecting part includes: a detector that detects electric field intensity of the electromagnetic wave pulse according to irradiation of probe light emitted from a light source of the pulsed light; and a delaying part that delays detection timing at which the detector detects the electromagnetic wave pulse by changing a temporal difference between a time the electromagnetic wave pulse reaches the detector and a time the probe light reaches the detecting part.

According to the inspection apparatus of the second aspect, the electric field intensity of the terahertz wave can be detected at arbitrary timing by providing the delaying part.

According to a third aspect, the inspection apparatus of the second aspect further includes a control part that controls the delaying part to obtain the detection timing at which electric field intensity of the electromagnetic wave pulse is maximal.

According to the inspection apparatus of the third aspect, the characteristic of the photoexcited carrier generation area is easily evaluated by detecting the electric field intensity at the timing at which the electric field intensity of the electromagnetic wave pulse is maximal.

According to a fourth aspect, the inspection apparatus of the second or third aspect further includes a time waveform constructing part that constructs a time waveform from electromagnetic wave intensity of an electromagnetic pulse detected by the detector at the plurality of pieces of detection timing.

According to the inspection apparatus of the fourth aspect, the characteristic of the photoexcited carrier generation area can be inspected by constructing the time waveform of the electromagnetic wave pulse.

According to a fifth aspect, the inspection apparatus of the fourth aspect further includes a spectrum analyzing part that performs a spectral analysis by performing a Fourier transformation based on the time waveform of the electromagnetic wave pulse, the time waveform being constructed by the time waveform constructing part.

According to the inspection apparatus of the fifth aspect, an abnormality of the substrate such as mixing of an impurity can be detected by performing the spectral analysis of the time waveform.

According to a sixth aspect, the inspection apparatus as in any one of the first to fifth aspects further includes a relatively-moving mechanism that moves the photo device relative to the irradiation part in a two-dimensional plane.

According to the inspection apparatus of the sixth aspect, various areas of the substrate can be inspected.

According to a seventh aspect, the inspection apparatus as in any one of the first to sixth aspects further includes a reverse bias applying circuit that applies a reverse bias voltage to a photo device formed in the photo device.

According to the inspection apparatus of the seventh aspect, the electric field intensity of the electromagnetic wave pulse generated by the irradiation of the pulsed light can be enhanced by applying the reverse bias voltage.

According to an eighth aspect, in the inspection apparatus as in any one of the first to seventh aspects, an optical axis of the pulsed light is obliquely incident to a light receiving surface from a light receiving surface side of the photo device.

According to a ninth aspect, in the inspection apparatus as in any one of the first to seventh aspects, an optical axis of the pulsed light is perpendicularly incident to a light receiving surface from a light receiving surface side of the photo device.

According to the inspection apparatus of the eighth and ninth aspects, the pulsed light easily reaches the photoexcited carrier generation area such as the depletion layer by irradiating the photoexcited carrier generation area with the pulsed light from the light receiving surface side. Accordingly, the electromagnetic wave pulse is easily generated to easily perform the inspection.

According to a tenth aspect, in the inspection apparatus of the ninth aspect, the detecting part detects an electromagnetic wave pulse emitted onto the light receiving surface side.

According to an eleventh aspect, in the inspection apparatus as in any one of the first to tenth aspects, the photo device is a crystalline silicon photovoltaic cell, and a wavelength of the pulsed light is equal to or lower than 1 micrometer.

According to a twelfth aspect, in the inspection apparatus as in any one of the first to eleventh aspects, the electromagnetic wave pulse generated in the photo device includes a terahertz wave having a frequency range of 0.01 terahertz to 10 terahertz.

According to a thirteenth aspect, in the inspection apparatus as in any one of the first to twelfth aspects, the irradiation part includes a femtosecond laser that emits pulsed light, and the inspection apparatus further includes: a control part that controls the irradiation part to change light intensity of the pulsed light; and a light intensity setting part that sets the light intensity of the pulsed light emitted from the femtosecond laser based on peak light intensity of the pulsed light when the light intensity is changed by the control part, the peak light intensity being obtained when the electric field intensity of the electromagnetic wave is maximal.

According to the inspection apparatus of the thirteenth aspect, the light intensity of the inspection pulsed light with which the photo device is irradiated can properly be set.

According to a fourteenth aspect, an inspection method for inspecting a photo device includes the steps of (a) irradiating the photo device with pulsed light; and (b) detecting an electromagnetic wave pulse, which is generated by the photo device according to the pulsed light irradiation.

According to a fifteenth aspect, in the inspection method of the fourteenth aspect, the (a) step is the step of irradiating a light receiving surface of a photo device with the pulsed light while changing light intensity of pulsed light emitted from a femtosecond laser, and the inspection method further includes the steps of: (c) acquiring peak light intensity of the pulsed light when the electric field intensity of the electromagnetic wave detected in the (b) step is maximal; and (d) detecting the electric field intensity of the electromagnetic wave pulse, generated by the photo device, with a detector by irradiating the photo device with pulsed light having light intensity, which is defined based on the peak light intensity acquired in the (c) step.

According to the inspection method of the fifteenth aspect, the light intensity of the inspection pulsed light with which the photo device is irradiated can properly be set.

According to a sixteenth aspect, in the inspection method of the fifteenth aspect, the (d) step is the step of irradiating the photo device with pulsed light having light intensity that does not exceed the peak light intensity.

According to the inspection method of the sixteenth aspect, a long service life and reduction of maintenance cost of the femtosecond laser can be achieved while the electric field intensity of the detected electromagnetic wave pulse is increased as large as possible.

According to a seventeenth aspect, the inspection method of the fifteenth or sixteenth aspect further includes the step of (e) applying a reverse bias voltage to the photo device when the (b) step is performed.

According to the inspection method of the seventeenth aspect, the electric field intensity of the terahertz wave can be amplified by applying the reverse bias voltage.

According to an eighteenth aspect, in the inspection method as in any one of the fifteenth to seventeenth aspects, the (b) step includes: (b-1) branching the pulsed light from the femtosecond laser into pump light oriented toward the photo device and probe light oriented toward the detector; and (b-2) changing an optical path length of one of a first optical path of the pump light and a second optical path of the probe light.

According to the inspection method of the eighteenth aspect, because the time waveform of the electromagnetic wave pulse can be restored, the timing at which the electric field intensity of the electromagnetic wave pulse is measured can well be determined.

According to a nineteenth aspect, in the inspection method of the eighteenth aspect, the (b) step further includes the step of (b-3) acquiring peak optical path length when the electric field intensity detected by the detector is maximal when the optical path length of one of the first optical path and the second optical path is changed in the (b-2) step, and the (a) step is the step of changing light intensity of the pulsed light while the optical path length of one of the first optical path and the second optical path is fixed to the peak optical path length.

According to the inspection method of the nineteenth aspect, a signal-noise ratio can be improved because the electric field intensity of the electromagnetic wave pulse detected by the detector is substantially maximal. Accordingly, because the electric field intensity can well be detected, the light intensity can properly be set.

According to a twentieth aspect, in the inspection method as in any one of the fifteenth to nineteenth aspects, the detector in the (b) step is constructed by a Schottky barrier diode.

According to the inspection method of the twentieth aspect, magnitude of the averaged electric field intensity of the electromagnetic wave pulse generated by the photo device can be detected by the use of the Schottky barrier diode as the detector. Accordingly, because the electric field intensity is acquired without restoring the time waveform, the light intensity can rapidly be set.

Therefore, the technology of inspecting the photoexcited carrier generation area of the photo device in the non-contact manner can be provided.

These and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a schematic configuration diagram of an inspection apparatus according to a first preferred embodiment;

FIG. 7 is a view illustrating a time waveform of a terahertz wave pulse constructed by a time waveform constructing part;

FIG. 8 is a view illustrating a spectral distribution of the terahertz wave pulse;

FIG. 11 is a schematic configuration diagram of an irradiation part and a detecting part of an inspection apparatus according to a second preferred embodiment;

FIG. 13 is a schematic configuration diagram of an inspection apparatus according to a fourth preferred embodiment;

FIG. 14 is a flowchart of an inspection of a photovoltaic cell panel 90 of the fourth preferred embodiment;

FIG. 17 is a view illustrating correlation data CD3 and a polygonal line graph of the correlation data CD3;

DESCRIPTION OF THE PREFERRED EMBODIMENTS

Hereinafter, preferred embodiments will be described in detail with reference to the drawings. Constituents are described in the preferred embodiments only by way of example, but the scope of the present invention is not limited to the constituents described in the preferred embodiments.

1. First Preferred Embodiment

Figure 2:
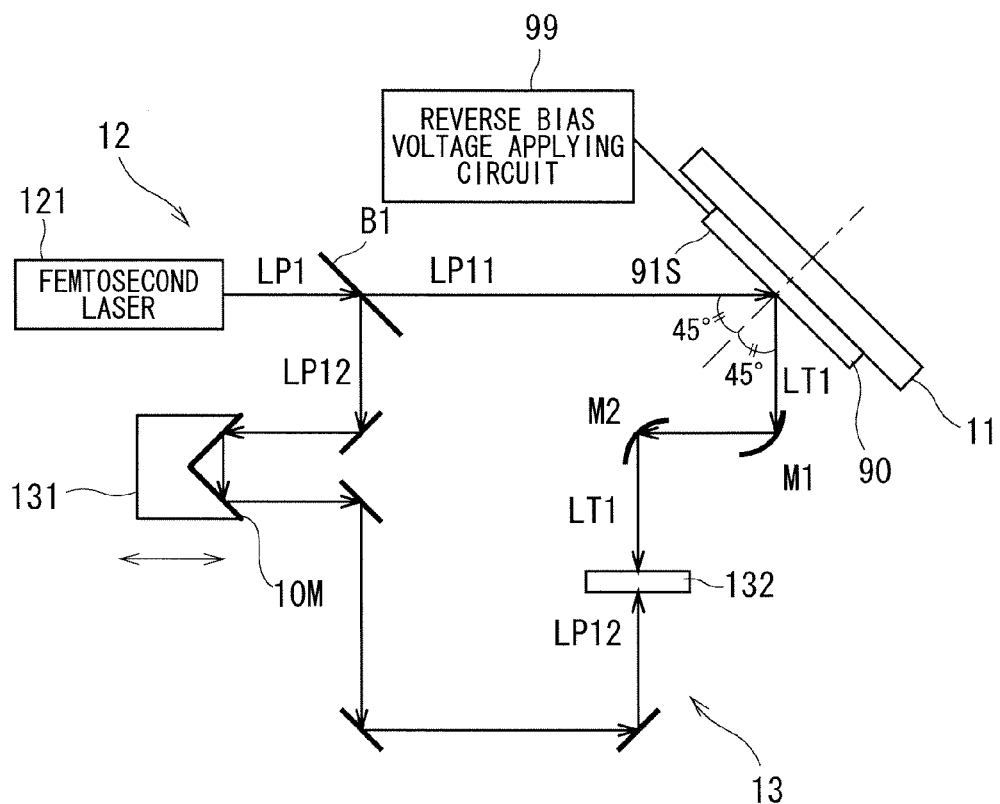
FIG. 2 is a schematic configuration diagram of an irradiation part and a detecting part in FIG. 1.

FIG. 1 is a schematic configuration diagram of an inspection apparatus 100 according to a first preferred embodiment. FIG. 2 is a schematic configuration diagram of an irradiation part 12 and a detecting part 13 shown in FIG. 1. The inspection apparatus 100 includes a configuration suitable to inspect a characteristic of a depletion layer of a photovoltaic cell panel 90. The photovoltaic cell panel 90 is a kind of a substrate in which a photo device is formed.

In the inspection apparatus 100, the substrate that becomes an inspection target is not limited to the photovoltaic cell panel 90. Any substrate including the photo device that converts light including visible light into a current may be used as an inspection object of the inspection apparatus 100. Examples of the photo device include image sensors such as a photo diode, a CMOS sensor and a CCD sensor in addition to the photovoltaic cell panel. In some of the image sensors, a light receiving element is formed in a portion that constitutes a rear surface side of the substrate, in which the photo device is formed, in a usage state. Even in such substrates, when a principal surface on a side on which the light is received in the usage state is placed as the light receiving surface on the inspection apparatus 100, a terahertz wave pulse LT1 can well be detected.

As described above, the photo device such as the photovoltaic cell has the pn junction in which a p-type semiconductor and an n-type semiconductor are coupled. A diffusion current in which electrons and holes are diffused and coupled is generated near the pn junction, thereby forming the depletion layer in which the numbers of electrons and holes are decreased near the pn junction. Because a force pulling the electrons and holes back to an n-type area and a p-type area is generated in this area, an electric field is generated in the photo device. In the case that the pn junction is irradiated with light having a certain level of energy (energy exceeding a forbidden band width), in the pn junction, a photoelectron moves onto the-n-type semiconductor side by the internal electric field while the hole left behind moves to the p-type semiconductor. In the photo device, the current is taken out to the outside through electrodes attached to the n-type semiconductor and the p-type semiconductor. Thus, the movements of the free electron and the free hole, which are generated when the depletion layer of the pn junction is irradiated with the light, are used as a DC power in the photo device.

The inventors found that an electromagnetic wave pulse having a specific wavelength is generated when the photo device is irradiated with pulsed light having a predetermined wavelength. This is attributed to the fact that the photoexcited carrier moves to generate the electromagnetic wave when the photoexcited carrier generation area such as the depletion layer is irradiated with the light. That is, the generated electromagnetic wave pulse reflects a characteristic of the photoexcited carrier generation area such as the depletion layer. Accordingly, the characteristic of the depletion layer of the pn junction can be inspected by analyzing the detected electromagnetic wave pulse. Based on the principle, the inspection apparatus 100 is configured to detect the electromagnetic wave pulse, which is generated when the photovoltaic cell panel 90 is irradiated with the pulsed light having the predetermined wavelength.

As illustrated in FIG. 1, the inspection apparatus 100 includes a stage 11, the irradiation part 12, the detecting part 13, a visible camera 14, a motor 15, a control part 16, a monitor 17, and a manipulation inputting part 18.

The photovoltaic cell panel 90 is fixed on the stage 11 by fixing unit (not illustrated). Examples of the fixing unit include a nipping tool that nips the substrate, an adhesive sheet, or a sucking hole made in a surface of the stage 11. However, any fixing unit may be used as long as the photovoltaic cell panel 90 can be fixed. In the first preferred embodiment, the stage 11 retains the photovoltaic cell panel 90 such that the irradiation part 12 and the detecting part 13 are disposed on a side of a light receiving surface 91S of the photovoltaic cell panel 90.

As illustrated in FIG. 2, the irradiation part 12 includes a femtosecond laser 121. For example, the femtosecond laser 121 emits pulsed light (pulsed light LP1) having a wavelength including visible light domain of 360 nm (nanometer) to him (micrometer). In the first preferred embodiment, the femtosecond laser 121 emits linearly-polarized pulsed light having a center wavelength of near 800 nm, a period of several kilohertz to hundreds megahertz, and a pulse width of about 10 to about 150 femtoseconds. The pulsed light having another wavelength domain (for example, a visible light wavelength such as a blue wavelength (450 to 495 nm) and a green wavelength (495 to 570 nm)) may be emitted.

The pulsed light LP1 emitted from the femtosecond laser 121 is split into two by a beam splitter B1. The photovoltaic cell panel 90 is irradiated with one of the pieces of split pulsed light (pulsed light LP11). At this point, the irradiation part 12 performs the irradiation of the pulsed light LP11 from the side of the light receiving surface 91S. The photovoltaic cell panel 90 is irradiated with the pulsed light LP11 such that an optical axis of the pulsed light LP11 is obliquely incident to the light receiving surface 91S of the photovoltaic cell panel 90. In the first preferred embodiment, an irradiation angle is set such that an incident angle becomes 45 degrees. However, the incident angle is not limited to 45 degrees, but the incident angle may properly be changed in a range of 0 degree to 90 degrees.

Figure 3:
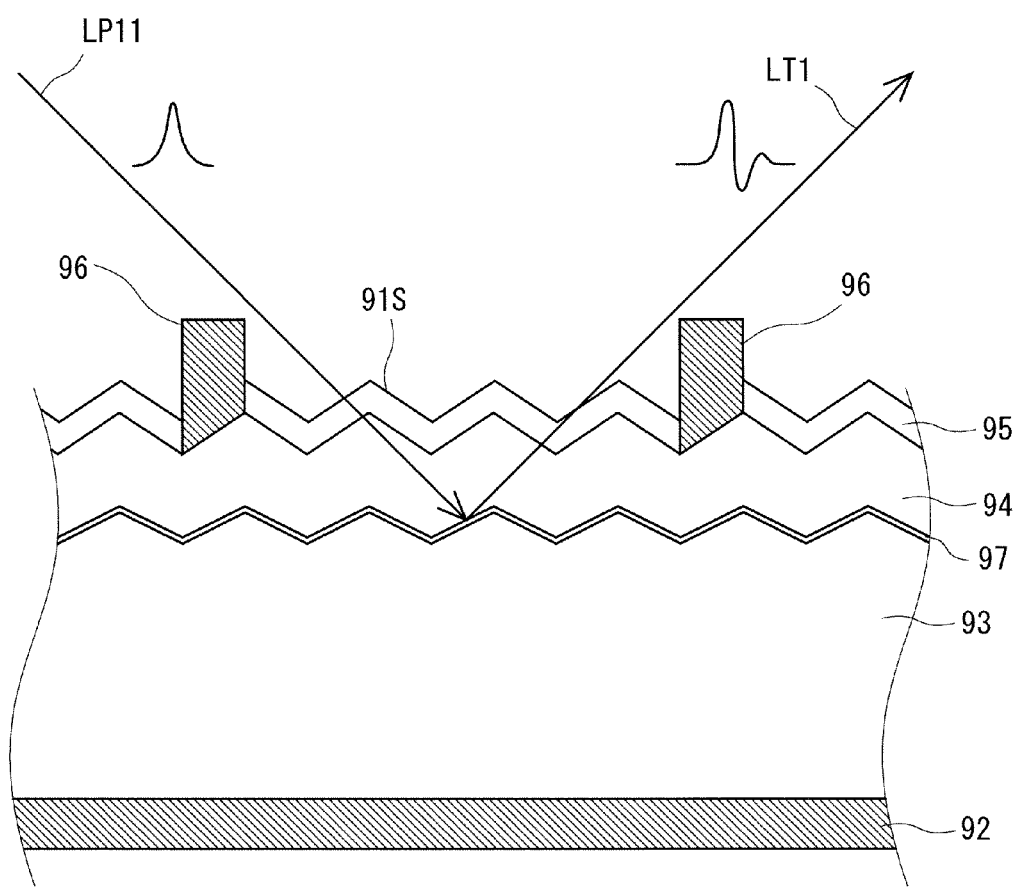
FIG. 3 is a schematic sectional view of a photovoltaic cell panel.
Figure 4:
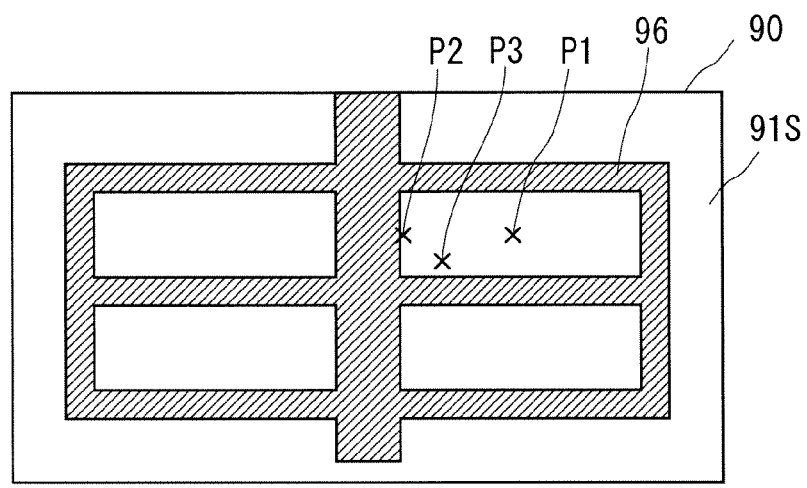
FIG. 4 is a plan view of the photovoltaic cell panel when viewed from a light receiving surface side.
Figure 5:
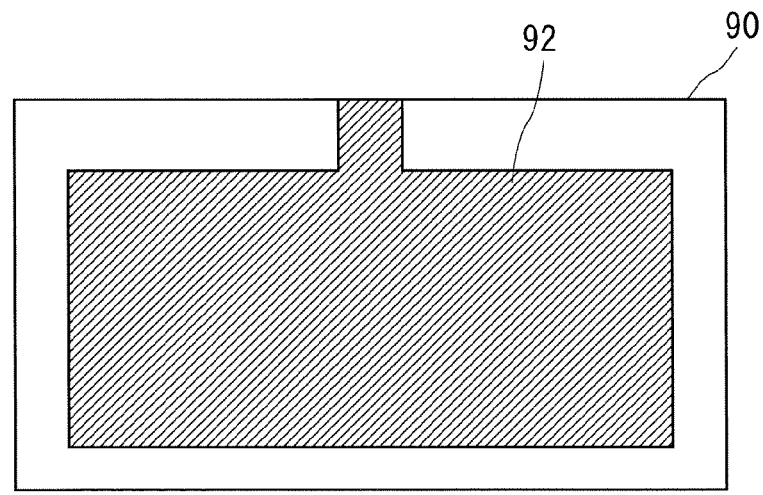
FIG. 5 is a plan view of the photovoltaic cell panel when viewed from a rear surface side.

FIG. 3 is a schematic sectional view of the photovoltaic cell panel 90. FIG. 4 is a plan view of the photovoltaic cell panel 90 when viewed from the light receiving surface side 91S. FIG. 5 is a plan view of the photovoltaic cell panel 90 when viewed from the rear surface side. The photovoltaic cell panel 90 is formed as a photovoltaic cell panel made of crystalline silicon. The photovoltaic cell panel 90 is formed as a crystalline silicon photovoltaic cell having a stacked structure, in which a planar rear surface electrode 92 made of aluminum, a p-type silicon layer 93, an n-type silicon layer 94, an antireflection film 95, and a lattice-shaped light receiving surface electrode 96 are sequentially stacked from a bottom. The antireflection film 95 is made of silicon oxide, silicon nitride, or titanium oxide. In the principal surfaces of the photovoltaic cell panel 90, the principal surface on the side on which the light receiving surface electrode 96 is provided constitutes the light receiving surface 91S. That is, the photovoltaic cell panel 90 is designed to generate an electric power by receiving the light from the side of the light receiving surface 91S. A transparent electrode may be used as the light receiving surface electrode 96. The inspection apparatus 100 may be applied to an inspection for a photovoltaic cell made of a material (such as amorphous silicon) except crystalline silicon. In the case of the amorphous silicon photovoltaic cell, generally an energy gap of 1.75 eV to 1.8 eV is larger than an energy gap of 1.2 eV of the crystalline silicon photovoltaic cell. In such cases, for example, the terahertz wave can well be generated in the amorphous silicon photovoltaic cell by setting the wavelength of the femtosecond laser 121 to 700 μm or less. In the same manner as described above, other semiconductor solar cell (such as CIGS-type or GaAS type solar cell) may be applied to.

The light receiving surface 91S of the photovoltaic cell panel 90 has a necessary texture structure in order to suppress a reflection loss of the light. Specifically, an irregularity of several micrometers to tens micrometers is formed by anisotropic etching, or a V-shape groove is formed by a mechanical method. Thus, the light receiving surface 91S of the photovoltaic cell panel 90 is generally formed such that lighting can efficiently be performed as much as possible. Accordingly, the pulsed light easily reaches a pn junction 97 when the photovoltaic cell panel 90 is irradiated with the pulsed light having the predetermined wavelength. For example, in the case of the photovoltaic cell panel, the light having the wavelength of 1 μm or less, which is of the wavelength domain of the visible light, can easily reach the pn junction 97.

A portion in which the p-type silicon layer 93 and the n-type silicon layer 94 are coupled constitutes the pn junction 97 in which the depletion layer is formed. The portion is irradiated with the pulsed light LP11 to generate the electromagnetic wave pulse, and the electromagnetic wave pulse is emitted to the outside. In the first preferred embodiment, the electromagnetic wave pulse detected by the detecting part 13 is an electromagnetic wave pulse (hereinafter referred to as a terahertz wave pulse LT1) having a frequency of 0.01 THz to 10 THz.

Referring to FIG. 2, the other piece of pulsed light split by the beam splitter B1 is incident as probe light LP12 to a detector 132 through a delaying part 131 and a mirror. The terahertz wave pulse LT1, which is generated according to the irradiation of the pulsed light LP11, is collected by paraboloid mirrors M1 and M2 and incident to the detector 132.

The detector 132 is constructed by a photoconductive switch. When the detector 132 is irradiated with the probe light LP12 while the terahertz wave is incident to the detector 132, a current corresponding to electric field intensity of the terahertz wave pulse LT1 is instantaneously passed through the detector 132. The current corresponding to the electric field intensity is converted into a digital amount through an I/V conversion circuit and an A/D conversion circuit. Therefore, the detecting part 13 detects the electric field intensity of the terahertz wave transmitted through the photovoltaic cell panel 90 according to the irradiation of the probe light. In the first preferred embodiment, the photoconductive switch is used as the detector 132. Alternatively, another element such as a nonlinear optical crystal may be used as the detector 132. The electric field intensity of the terahertz wave pulse LT1 may be detected with a Schottky barrier diode.

The delaying part 131 is an optical element that continuously changes a time necessary for the probe light LP12 to reach the detector 132 from the beam splitter B1. The delaying part 131 is fixed to a moving stage (not illustrated) that moves in an incident direction of the probe light LP12. The delaying part 131 includes a folding mirror 10M that folds the probe light LP12 in the incident direction. Under the control of the control part 16, the delaying part 131 drives the moving stage to move the folding mirror 10M, thereby precisely changing an optical path length of the probe light LP12. Therefore, the delaying part 131 changes a temporal difference between a time necessary for the terahertz wave pulse LT1 to reach the detecting part 13 and a time necessary for the probe light LP12 to reach the detecting part 13. Accordingly, the delaying part 131 changes the optical path length of the probe light LP12, which allows the detecting part 13 (detector 132) to delay timing (detection timing or sampling timing) at which the electric field intensity of the terahertz wave pulse LT1 is detected.

The delaying part 131 may change the time necessary for the terahertz wave pulse LT1 to reach the detecting part 13 and the time necessary for the probe light to reach the detecting part 13 in another mode. For example, an electrooptic effect may be used. That is, an electrooptic element, in which a refractive index is changed by changing an applied voltage, may be used as the delay element. Specifically, an electrooptic element disclosed in Japanese Patent Application Laid-Open No. 2009-175127 can be used. A length of an optical path (first optical path) of the pump light LP11 may be changed. In this case, the time necessary for the terahertz wave pulse LT1 to reach the detector 132 and the time necessary for the probe light LP12 to reach the detector 132 can relatively be deviated. Accordingly, the detection timing of the electric field intensity of the terahertz wave pulse LT1 can be delayed in the detector 132.

A reverse bias voltage applying circuit 99 that applies a reverse bias voltage between the rear surface electrode 92 and the light receiving surface electrode 96 during the inspection is connected to the photovoltaic cell panel 90. The depletion layer of the pn junction 97 can be enlarged by applying the reverse bias voltage between the electrodes. Therefore, the electric field intensity of the terahertz wave pulse LT1 detected by the detector 132 is enlarged, so that detection sensitivity of the terahertz wave pulse LT1 can be improved in the detecting part 13. However, the reverse bias voltage applying circuit 99 may be omitted.

Referring to FIG. 1, the visible camera 14 is constructed by a CCD camera, and the visible camera 14 includes an LED or a laser device as a light source. The visible camera 14 takes a picture of the whole photovoltaic cell panel 90 or a position irradiated with the pulsed light LP11. The image data captured by the visible camera 14 is transmitted to the control part 16.

The motor 15 drives an X-Y table (not illustrated) that moves the stage in a two-dimensional plane. The motor 15 drives the X-Y table to relatively move the photovoltaic cell panel 90 retained by the stage 11 with respect to the irradiation part 12. The inspection apparatus 100 can move the photovoltaic cell panel 90 to an arbitrary position in the two-dimensional plane using the motor 15. The inspection apparatus 100 can perform the inspection by irradiating a wide range (inspection target area) of the photovoltaic cell panel 90 with the pulsed light LP11 using the motor 15. Moving unit for moving the irradiation part 12 and the detecting part 13 in the two-dimensional plane may be provided instead of moving the photovoltaic cell panel 90, or moving unit for moving the irradiation part 12 and the detecting part 13 in the two-dimensional plane while the moving photovoltaic cell panel 90 may be provided. In such cases, the terahertz wave pulse LT1 can be detected in each area of the photovoltaic cell panel 90. An operator may manually move the stage 11 while the motor 15 is omitted.

The control part 16 includes a configuration as a general computer (not illustrated) that includes a CPU, a ROM, a RAM, and an auxiliary storing part (such as a hard disk). The control part 16 is connected to the femtosecond laser 121 of the irradiation part 12, the delaying part 131 and the detector 132 of the detecting part 13, and the motor 15, and the control part 16 controls operations of these parts and receives pieces of data from these parts. Specifically, the control part 16 receives data relating to the electric field intensity of the terahertz wave pulse LT1 from the detector 132. The control part 16 controls a movement of a moving stage (not illustrated) that moves the delaying part 131, and receives data relating to the position of the delaying part 131, such as a moving distance of the folding mirror 10M, from a linear scale provided in the moving stage.

The control part 16 includes a time waveform constructing part 21, a spectrum analyzer 23, and an image generator 25, and the control part 16 causes each part to perform various pieces of calculation processing. Each part is a function, which is implemented such that the CPU is operated according to a program. A part of or all the functions may be implemented by the CPU included in another computer or a dedicated calculation circuit.

Based on the electric field intensity detected by the detecting part 13 (detector 132), the time waveform constructing part 21 constructs a time waveform of the terahertz wave with respect to the terahertz wave pulse LT1 generated in the photovoltaic cell panel 90. Specifically, the folding mirror 10M of the delaying part 131 is moved to change the optical path length (the length of the first optical path) of the probe light LP12, thereby the time necessary for the probe light to reach the detector 132. Therefore, the timing at which the electric field intensity of the terahertz wave pulse LT1 is detected is changed in the detector 132. The electric field intensity of the terahertz wave pulse LT1 is detected at pieces of detection timing different from each other, thereby constructing the time waveform of the terahertz wave pulse LT1.

The spectrum analyzing part 23 performs a spectral analysis to the photovoltaic cell panel 90 that is of the inspection object based on the time waveform of the terahertz wave pulse LT1. Particularly, the spectrum analyzing part 23 acquires an amplitude intensity spectrum relating to the frequency by performing a Fourier transformation to the time waveform of the terahertz wave pulse LT1, which is generated according to the irradiation of the pulsed light LP11.

The image generator 25 generates an image, in which a distribution of the electric field intensity of the terahertz wave pulse LT1 generated by the irradiation of the pulsed light LP1 is visualized, with respect to an inspection target area (part or a whole of the photovoltaic cell panel 90) of the photovoltaic cell panel 90. Specifically, an electric field intensity distribution image is generated by superimposing a color or a pattern corresponding to the electric field intensity at each measurement position on a visible light image of the light receiving surface 91S of the photovoltaic cell panel 90, which is captured by the visible camera 14.

The monitor 17 and the manipulation inputting part 18 are connected to the control part 16. The monitor 17 is a display device such as a liquid crystal display, and the monitor 17 displays various pieces of image information to the operator. For example, the image of the light receiving surface 91S of the photovoltaic cell panel 90, in which the picture is taken by the visible camera 14, the time waveform of the terahertz wave pulse LT1, which is constructed by the time waveform constructing part 21, an analysis result of the spectrum analyzer 23, and the electric field intensity distribution image generated by the image generator 25 are displayed on the monitor 17. A GUI (Graphical User Interface) screen is also displayed on the monitor 17 in order to set an inspection condition.

The manipulation inputting part 18 is constructed by various input devices such as a mouse and a keyboard. The operator can perform a predetermined manipulation input through the manipulation inputting part 18. The monitor 17 may act as the manipulation inputting part 18 such that the monitor 17 is constructed by a touch panel.

The configuration of the inspection apparatus 100 are described above. A specific operation of the inspection apparatus 100 in inspecting the photovoltaic cell panel 90 will be described below.

The inspection apparatus 100 of the first preferred embodiment is configured to be able to perform two kinds of inspections. A first inspection is (1) an inspection (hereinafter referred to as an inspection (1)) based on the time waveform of the terahertz wave pulse LT1. The time waveform of the terahertz wave pulse LT1 generated by irradiating a specific area (inspection position) with the pulsed light LP11 is constructed in the inspection (1). The spectral analysis is performed based on the constructed time waveform (terahertz time domain spectroscopy (THz-TDS)). The formation of the depletion layer in the specific area of the photovoltaic cell panel 90 or an impurity can be inspected by the analysis.

A second inspection is (2) an inspection (hereinafter referred to as an inspection (2)) based on the electric field intensity distribution of the terahertz wave pulse LT1 with respect to the whole of the photovoltaic cell panel 90. In the inspection (2), the electric field intensity of the terahertz wave pulse LT1 generated by the irradiation of the pulsed light LP11 is measured in each area on the photovoltaic cell panel 90. Therefore, a shape failure portion of the depletion layer or a crystal defect of the polycrystalline silicon can be specified in the inspection target area of the photovoltaic cell panel 90. Hereinafter, the inspection (1) is first described, and then the inspection (2) is described.

<Inspection (1)>

Figure 6:
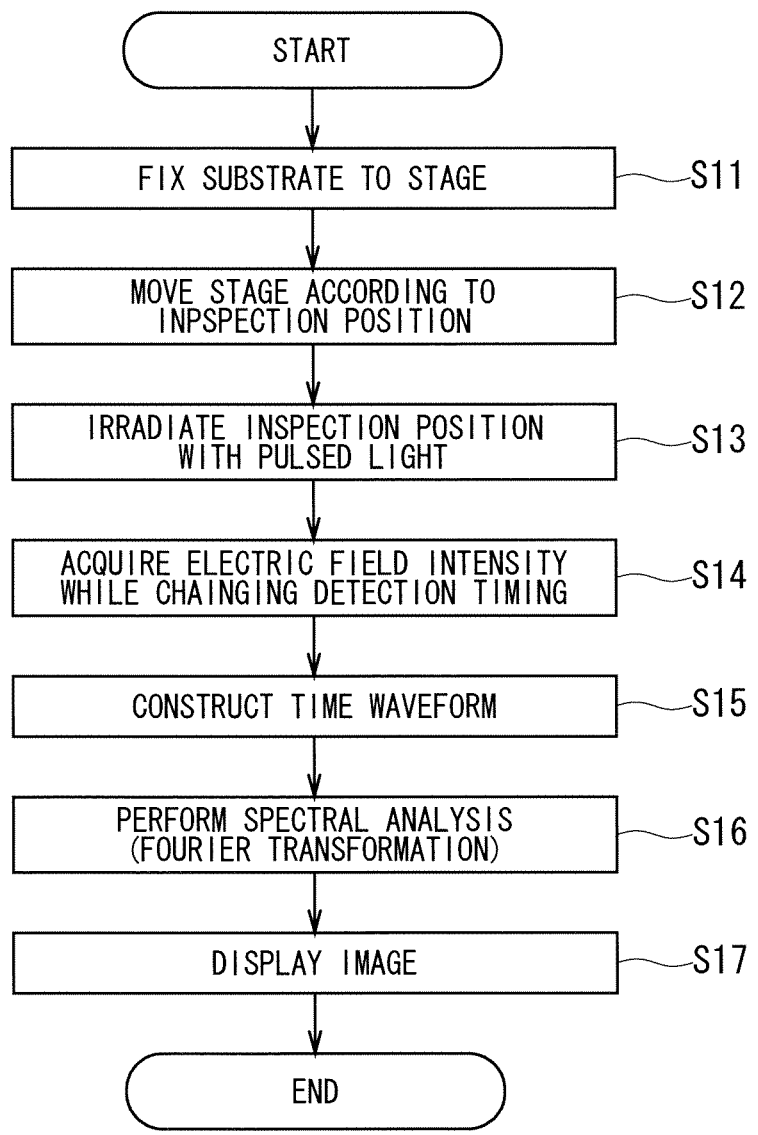
FIG. 6 is a flowchart of an operation of the inspection apparatus in an inspection (1)

FIG. 6 is a flowchart of the operation of the inspection apparatus 100 in the inspection (1). In the following description, unless otherwise noted, it is assumed that each operation of the inspection apparatus 100 is controlled by the control part 16. The flowchart is illustrated in FIG. 6 by way of example. Accordingly, depending on operation contents, plural processes may concurrently be performed, or a sequence of plural processes may properly be changed.

The photovoltaic cell panel 90 that constitutes the inspection target is fixed to the stage 11 (Step S11). In Step S11, the operator may carry the photovoltaic cell panel 90 to the stage 11, or a conveying device (not illustrated) may carry the photovoltaic cell panel 90 to the stage 11. At this point, as described above, the photovoltaic cell panel 90 is placed such that the light receiving surface 91S of the photovoltaic cell panel 90 is irradiated with the pulsed light LP11.

When the photovoltaic cell panel 90 is fixed to the stage 11, the inspection apparatus 100 moves the photovoltaic cell panel 90 according to the inspection position (Step S12). Using the manipulation inputting part 18, the operator previously inputs the inspection position as data (coordinate data) relating to the position on the photovoltaic cell panel 90 to be inspected. In order to irradiate the inspection position with the pulsed light LP11, the control part 16 drives the motor 15 to move the stage 11 based on the coordinate data. The operator may move the stage 11 to move the photovoltaic cell panel 90 according to the inspection position.

When the movement of the photovoltaic cell panel 90 is completed, the inspection apparatus 100 starts to irradiate the inspection position of the photovoltaic cell panel 90 with the pulsed light LP11 (Step S13). The inspection apparatus 100 detects the electric field intensity of the terahertz wave pulse LT1 generated by the irradiation of the pulsed light LP11 (Step S14). In Step S14, when the electric field intensity of the terahertz wave pulse LT1 is detected, the control part 16 controls the delaying part 131 to delay the timing at which the probe light LP12 reaches the detector 132. Therefore, the electric field intensity of the terahertz wave pulse LT1 is detected at plural pieces of detection timing different from each other. In detecting the terahertz wave pulse LT1, the reverse bias voltage may be applied between the electrodes of the photovoltaic cell panel 90 by driving the reverse bias voltage applying circuit 99.

When the inspection is completed, the inspection apparatus 100 constructs the time waveform of the terahertz wave pulse LT1 based on the detection result of the electric field intensity acquired in Step S14. Specifically, the time waveform constructing part 21 constructs the time waveform by plotting a value of the electric field intensity detected in Step S14 on a graph.

FIG. 7 is a view illustrating the time waveform of the terahertz wave pulse LT1 constructed by the time waveform constructing part 21. In FIG. 7, a horizontal axis indicates the time, and a vertical axis indicates the electric field intensity. A lower stage of FIG. 7 conceptually illustrates plural pieces of probe light LP12 in which the timing (pieces of detection timing t1 to t8) at which the probe light LP12 reaches the detector 132 is varied by the delaying part 131. In FIG. 7, a time waveform 41 indicated by a solid line corresponds to the terahertz wave pulse LT1 detected in an inspection position P2 in FIG. 4, and a time waveform 42 indicated by a broken line corresponds to the terahertz wave pulse LT1 detected in an inspection position P1 shown in FIG. 4.

For example, when the inspection position P2 is irradiated with the pulsed light LP11, the terahertz wave pulse LT1 indicating the time waveform 41 in FIG. 7 comes repeatedly to the detector 132 in a predetermined period. At this point, when the delaying part 131 is adjusted such that the probe light reaches the detector 132 in detection timing t1, the detector 132 detects the electric field intensity of a value E1. When the detection timing is delayed to t2 to t8 by adjusting the delaying part 131, the detecting part 13 detects the pieces of electric field intensity of values E2 to E8, respectively. In this way, the electric field intensity of the terahertz wave pulse LT1 is measured while the detection timing is finely changed, and the acquired electric field intensity values are plotted on the graph along a temporal axis to construct the time waveform 41 of the terahertz wave pulse LT1. The time waveform 42 is constructed in the same way with respect to the terahertz wave pulse LT1 measured in the inspection position P1.

Therefore, the characteristic of the depletion layer of the pn junction 97 can be inspected in each of the inspection positions P1 and P2 by constructing the time waveforms 41 and 42. For example, the shape failure of the depletion layer can be detected by inspecting the existence or non-existence of the detection of the terahertz wave pulse or by comparing an amplitude of the electric field intensity of the constructed time waveform to a standard value. The shape failures of various photoexcited carrier generation areas of the photovoltaic cell can be detected through the same processing.

Referring to FIG. 6, when the time waveform is acquired, the inspection apparatus 100 performs the spectral analysis (Step S16). Specifically, based on the time waveform acquired in Step S15, the spectrum analyzer 23 performs the Fourier transformation to acquire the spectral distribution of the terahertz wave pulse LT1.

FIG. 8 is a view illustrating the spectral distribution of the terahertz wave pulse LT1. In FIG. 8, a vertical axis indicates spectral intensity and a horizontal axis indicates a frequency. In FIG. 8, a spectral distribution 51 of the terahertz wave pulse LT1 detected in the inspection position P2 in FIG. 4 is indicated by a solid line. A spectral distribution 52 of the terahertz wave pulse LT1 detected in the inspection position P1 in FIG. 4 is indicated by a broken line. In the first preferred embodiment, the strong spectral intensity is detected in the frequency range of 0.1 THz to 1 THz.

The characteristic of the depletion layer of the pn junction 97 formed in each of the inspection positions P1 and P2 can be inspected by acquiring the spectral distributions 51 and 52. For example, that the impurity absorbing the specific frequency is included in the depletion layer formed in the inspection position P1 can be detected when spectral intensity at a specific frequency indicated by an arrow is significantly lower than a reference value (not illustrated) in the spectral distribution 52. A kind or a concentration of the impurity can be estimated from the absorbed frequency. The spectral analysis in Step S16 may be eliminated.

Referring to FIG. 6, when the spectral analysis is completed, the inspection apparatus 100 displays the image indicating the inspection result on the monitor 17 (Step S17). Specifically, for example, the time waveform (see FIG. 7) of the terahertz wave pulse LT1 acquired in Step S15 and the spectral distribution (see FIG. 8) acquired in Step S16 are displayed as the analysis result on the monitor 17. The inspection (1) is described above.

<Inspection (2)>

Figure 9:
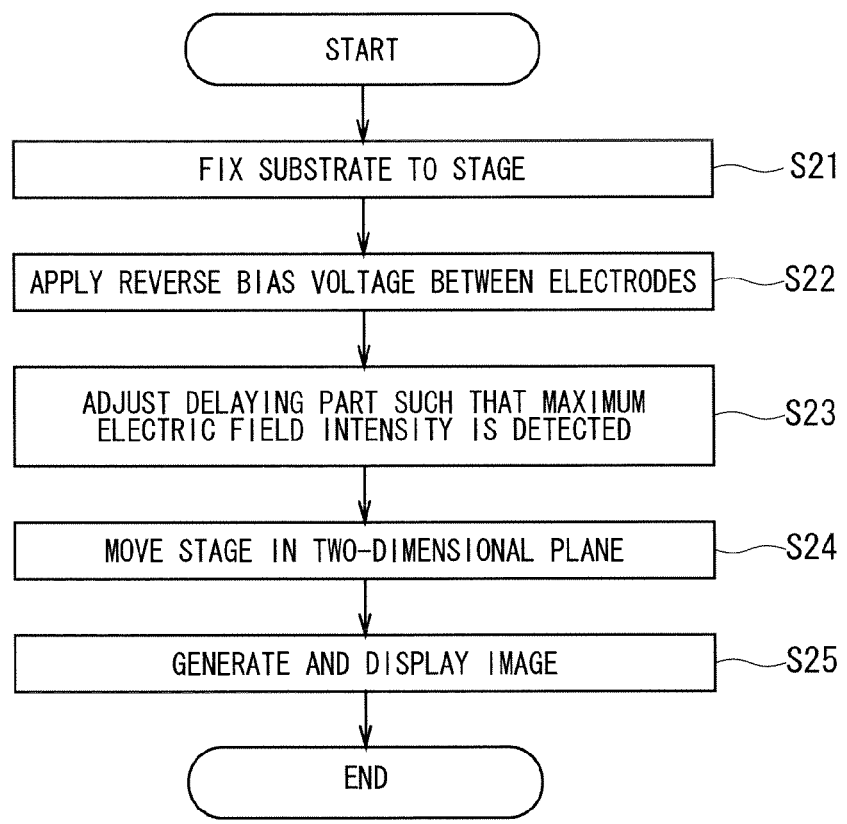
FIG. 9 is a flowchart of an operation of the inspection apparatus in an inspection (2)

FIG. 9 is a flowchart of the operation of the inspection apparatus 100 in the inspection (2). In the inspection (1), the restoration and spectral analysis of the time waveform of the terahertz wave pulse LT1 generated by the irradiation of the pulsed light LP11 are performed to the specific area on the photovoltaic cell panel 90. On the other hand, in the inspection (2), a state of the photoexcited carrier generation area is inspected with respect to the whole surface of the photovoltaic cell panel 90.

The photovoltaic cell panel 90 is fixed to the stage 11 (Step S21). The process in Step S21 is identical to that in Step S11 of the inspection (1) in FIG. 6. The reverse bias voltage is applied between the rear surface electrode 92 and the light receiving surface electrode 96 of the photovoltaic cell panel 90 (Step S22). It is not always necessary to apply the reverse bias voltage, but the application of the reverse bias voltage may be omitted.

The inspection apparatus 100 adjusts the delaying part 131 such that the electric field intensity of the terahertz wave pulse detected by the detector 132 is maximal (Step S23). Specifically, the control part 16 adjusts the delaying part 131 to change the timing at which the probe light LP12 reaches the detector 132. At this point, the detection timing is adjusted such that the electric field intensity of the terahertz wave pulse LT1 detected by the detector 132 is maximal.

For example, as illustrated in FIG. 7, in the terahertz wave pulse LT1 indicating the time waveform 41, the electric field intensity of the terahertz wave pulse LT1 is maximal at the detection timing t3. That is, the maximum value of the electric field intensity of the terahertz wave pulse LT1 is detected by adjusting the delaying part 131 according to the detection timing t3. Even if another portion of the photovoltaic cell panel 90 is irradiated with the pulsed light LP1, the electric field intensity value of the terahertz wave pulse LT1 is substantially maximal as long as the detection is performed at the detection timing t3. Thus, the maximum value of the electric field intensity of the terahertz wave pulse LT1 is detected to facilitate the detection of the electric field intensity, and the detection sensitivity of the terahertz wave pulse LT1 can be improved.

The inspection apparatus 100 drives the motor 15 to move the photovoltaic cell panel 90 in the two-dimensional plane (Step S24). At this point, the photovoltaic cell panel 90 is irradiated with the pulsed light LP11, and the electric field intensity of the generated terahertz wave pulse LT1 is detected. Therefore, the electric field intensity distribution is acquired with respect to the inspection target area on the photovoltaic cell panel 90. As to the movement of the photovoltaic cell panel 90, for example, after the photovoltaic cell panel 90 is moved in a main scanning direction to inspect the inspection target area from one end portion to the other end portion, the photovoltaic cell panel 90 is moved (deviated) in a sub-scanning direction by a necessary distance, and moved in the main scanning direction again. The electric field intensity of the terahertz wave pulse LT1 is acquired with respect to the inspection target area of the photovoltaic cell panel 90 by repeating the movement of the photovoltaic cell panel 90.

When acquiring the electric field intensity of the terahertz wave pulse LT1, the inspection apparatus 100 generates the image indicating the electric field intensity distribution, and displays the image on the monitor 17 (Step S25).

Figure 10:
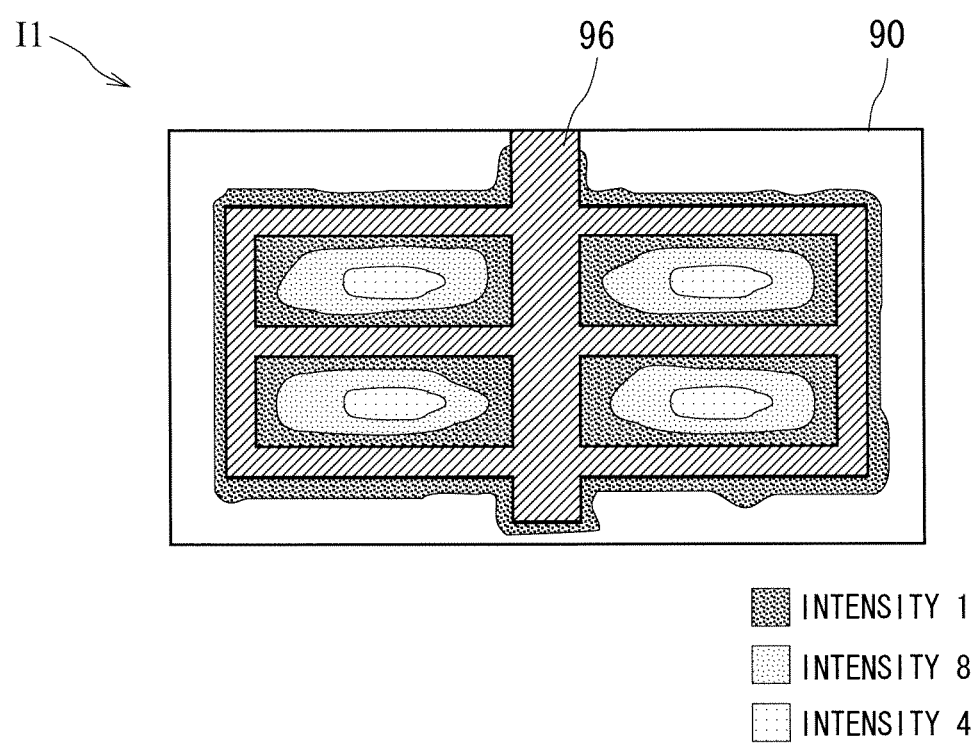
FIG. 10 is a view illustrating an example of an electric field intensity distribution image displayed on a monitor.

FIG. 10 is a view illustrating an example of an electric field intensity distribution image I1 displayed on the monitor 17. In the electric field intensity distribution image I1, the image indicating the photovoltaic cell panel 90 in which the picture is taken with the visible camera 14 is colored according to magnitude of the electric field intensity detected in each inspection position. In FIG. 10, for the sake of convenience, a distribution of the magnitude of the electric field intensity is illustrated by changing hatching. A value (10, 8, or 4) of the electric field intensity is a relative value. In FIG. 10, the electric field intensity distribution is illustrated only by three-stage electric field intensity. Alternatively, the electric field intensity distribution may be illustrated by finely segmenting the electric field intensity.

As illustrated in FIG. 10, in the photovoltaic cell panel 90, the electric field intensity is maximal around the light receiving surface electrode 96, and the electric field intensity is decreased with distance from the light receiving surface electrode 96. A formation status of the photoexcited carrier generation area can be recognized at once with respect to the inspection target area of the photovoltaic cell panel 90 by generating and displaying the electric field intensity distribution image I1. The crystal defect of the polycrystalline silicon and the like can also be estimated from an abnormality of the detected electric field intensity.

In the first preferred embodiment, the detector 132 detects the electric field intensity at the detection timing at which the electric field intensity of the terahertz wave pulse LT1 is maximal. Alternatively, the detector 132 may detect the electric field intensity at another piece of detection timing.

An image of a distribution of the electric field intensity detected by the irradiation of each of the pieces of pulsed light having plural wavelength domains may be formed. At this point, it is also conceivable that the distribution can be recognized in each wavelength domain in the same image by performing color coding and a combination of the wavelength domains.

In the first preferred embodiment, only the electric field intensity is detected at one time point of the terahertz wave pulse LT1. Alternatively, for example, as described in the inspection (1), the time waveform of the terahertz wave pulse LT1 generated in each inspection position in the inspection target area may be constructed by controlling the delaying part 131. The Fourier transformation is performed to the acquired time waveform to acquire the spectral distribution, which allows the electric field intensity distribution to be obtained in each specific frequency space. The image in which the electric field intensity distribution is visualized by the color coding and the like may be generated.

According to the inspection apparatus 100 of the first preferred embodiment, the photoexcited carrier generation area formed in the photovoltaic cell panel 90 is irradiated with the pulsed light, and the terahertz wave pulse generated by the irradiation of the pulsed light is detected. Therefore, the characteristic of the depletion layer can be inspected. Accordingly, because the inspection can be performed in the non-contact state, a breakdown of the photovoltaic cell panel 90, efficient failure determination, and prevention of a damage accident caused by the contact can be achieved.

2. Second Preferred Embodiment

In the first preferred embodiment, the optical axis of the pulsed light LP11 is obliquely (incident angle 45°) incident to the light receiving surface 91S of the photovoltaic cell panel 90. However, the incident angle is not limited to the 45 degrees.

FIG. 11 is a schematic configuration diagram of an irradiation part 12A and a detecting part 13A of an inspection apparatus 100A according to a second preferred embodiment. Hereinafter, an element having the same function as that of the constituent of the inspection apparatus 100 of the first preferred embodiment is designated by the same numeral, and the description is omitted.

In the inspection apparatus 100A, the pulsed light LP1 emitted from the femtosecond laser 121 is also split into the pulsed light LP11 and the probe light LP12 by the beam splitter B1. However, in the second preferred embodiment, the split pulsed light LP11 is transmitted through a transparent conductive film substrate (ITO) 19, and perpendicularly incident to the light receiving surface 91S of the photovoltaic cell panel 90. In the terahertz wave pulse LT1 generated by the irradiation of the pulsed light LP11, the terahertz wave pulse LT1 emitted onto the side of the light receiving surface 91S is reflected by the transparent conductive substrate 19 and incident to the detector 132 through the lens and the like.

The inspection apparatus 100A including the irradiation part 12A and the detecting part 13A can also detect the terahertz wave pulse LT1 generated by the irradiation of the pulsed light LP11. Accordingly, similarly to the inspection apparatus 100 of the first preferred embodiment, the inspection apparatus 100A can inspect the characteristic of the photoexcited carrier generation area such as the depletion layer of the photovoltaic cell panel 90 in the non-contact state.

3. Third Preferred Embodiment

In the second preferred embodiment, the terahertz wave pulse LT1 emitted onto the side of the light receiving surface 91S is detected. Alternatively, the terahertz wave pulse LT1 transmitted onto the rear surface side of the photovoltaic cell panel 90 may be detected.

Figure 12:
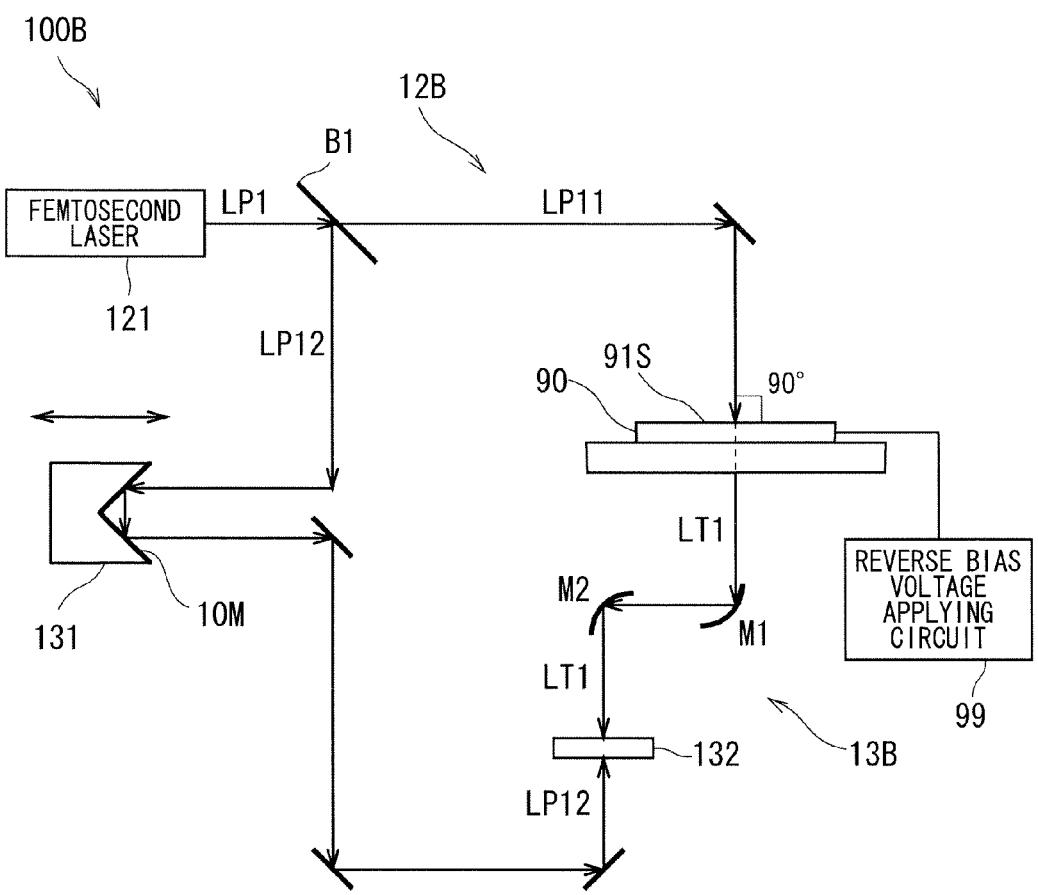
FIG. 12 is a schematic configuration diagram of an irradiation part and a detecting part of an inspection apparatus according to a third preferred embodiment.

FIG. 12 is a schematic configuration diagram of an irradiation part 12B and a detecting part 13B of an inspection apparatus 100B according to a third preferred embodiment. In the inspection apparatus 100B, the pulsed light LP1 emitted from the femtosecond laser 121 is also split into the pulsed light LP11 and the probe light LP12 by the beam splitter B1. In the third preferred embodiment, the pulsed light LP11 is perpendicularly incident to the light receiving surface 91S of the photovoltaic cell panel 90. In the terahertz wave pulse LT1 generated by the irradiation of the pulsed light LP11, the terahertz wave pulse LT1 emitted (transmitted) onto the rear surface side of the photovoltaic cell panel 90 is incident to the detector 132 through the paraboloid mirrors M1 and M2 and the like.

The inspection apparatus 100B including the irradiation part 12B and the detecting part 13B can also detect the terahertz wave pulse LT1 generated by the irradiation of the pulsed light LP11. Accordingly, similarly to the inspection apparatus 100 of the first preferred embodiment, the inspection apparatus 100B can inspect the characteristic of the photoexcited carrier generation area of the photovoltaic cell panel 90 in the non-contact state.

4. Fourth Preferred Embodiment

In the inspection apparatuses 100, 100A, and 100B of the preferred embodiments, the femtosecond laser 121 is used to emit the pulsed light. At this point, the light intensity of the pulsed light emitted from the femtosecond laser 121 largely influences a lifetime of the femtosecond laser 121. Accordingly, desirably the light intensity is weakened as much as possible in order to extend the lifetime (continuous operating time) of the femtosecond laser 121 or to reduce maintenance cost. However, in order to enhance the intensity of the electromagnetic wave intensity generated in the photo device, it is necessary that the pulsed light having a necessary level of light intensity be emitted from the femtosecond laser 121. Therefore, desirably the light intensity of the pulsed light is optimized in order that the photo device is properly inspected while the cost necessary to maintain the femtosecond laser 121 is suppressed.

A technology, in which the light intensity of the pulsed light is properly set when the photo device is irradiated with the pulsed light to perform the inspection, is provided in a fourth preferred embodiment.

<4.1. Configuration and Function>

FIG. 13 is a schematic configuration diagram of an inspection apparatus 100C according to the fourth preferred embodiment. In the inspection apparatus 100C, the control part 16 of the inspection apparatus 100 in FIG. 1 includes a light intensity setting part 27. The light intensity setting part 27 is a function, which is implemented such that the CPU included in the control part 16 is operated according to a program. However, the light intensity setting part 27 may be a function implemented by a CPU included in another computer, or the light intensity setting part 27 may be constructed by a dedicated calculation circuit.

The light intensity setting part 27 is one that sets intensity of light emitted from a laser beam source. The control part 16 causes the femtosecond laser 121 (laser device) to emit a laser beam (pulsed light) having the light intensity set by the light intensity setting part 27.

<4.2. Inspection of Photo Device>

FIG. 14 is a flowchart of an inspection of the photovoltaic cell panel 90 of the fourth preferred embodiment. Unless otherwise noted, it is assumed that the operation of the inspection apparatus 100C is controlled by the control part 16. The flowchart is illustrated in FIG. 14 by way of example. Accordingly, depending on operation contents, plural processes may concurrently be performed, or a sequence of plural processes may properly be changed. In the inspection apparatus 100C, when the photovoltaic cell panel 90 that is of the photo device is inspected, the light intensity of the pulsed light emitted from the femtosecond laser 121 is optimized (Steps S11A to S19A). The photovoltaic cell panel 90 is inspected by irradiating the photovoltaic cell panel 90 with the pulsed light having the optimum light intensity (Step S20A).

The configuration of the inspection apparatus 100C is described above. A photo device inspecting method in which the inspection apparatus 100C is used will be described in detail.

<1.2. Inspection of Photo Device>

FIG. 14 is the flowchart of the inspection of the photovoltaic cell panel 90 that is of the photo device. Unless otherwise noted, it is assumed that the operation of the inspection apparatus 100C is controlled by the control part 16. The flowchart is illustrated in FIG. 14 by way of example. Accordingly, depending on operation contents, plural processes may concurrently be performed, or a sequence of plural processes may properly be changed. In the inspection apparatus 100C, when the photovoltaic cell panel 90 that is of the photo device is inspected, the light intensity of the pulsed light emitted from the femtosecond laser 121 is optimized (Steps S11A to S19A). The photovoltaic cell panel 90 is inspected by irradiating the photovoltaic cell panel 90 with the pulsed light having the optimum light intensity (Step S20A).

First the photo device (photovoltaic cell panel 90) that is of the inspection target is placed on the stage 11 (Step S11A). In Step S11A, the operator may carry the photovoltaic cell panel 90 to the stage 11, or the conveying device (not illustrated) may carry the photovoltaic cell panel 90 to the stage 11. At this point, as described above, the photovoltaic cell panel 90 is placed on the stage 11 such that the light receiving surface 91S of the photovoltaic cell panel 90 is irradiated with the pulsed light (pump light LP11).

When the photovoltaic cell panel 90 is fixed to the stage 11, the inspection apparatus 100C moves the photovoltaic cell panel 90 by driving the motor 15 such that an arbitrary position of the photovoltaic cell panel 90 is irradiated with the pulsed light. The position irradiated with the pulsed light may be specified by previously-set coordinate data, or the operator may properly input and assign the position irradiated with the pulsed light through the manipulation inputting part 18. Alternatively, the predetermined position of the photovoltaic cell panel 90 may be irradiated with the pulsed light such that the operator manually moves the stage 11.

Then the inspection apparatus 100C performs the terahertz time domain spectroscopy (THz-TDS) to restore the time waveform of the terahertz wave, which is generated when the predetermined position of the photovoltaic cell panel 90 is irradiated with the pulsed light (pump light LP11) (Step S12A). More particularly, the inspection apparatus 100C controls the delaying part 131 while the photovoltaic cell panel 90 is irradiated with the pulsed light, whereby the electric field intensity of the terahertz wave pulse is detected while the detection timing of the electric field intensity is changed in the detector 132. At this point, the reverse bias voltage may be applied to the photovoltaic cell panel 90 by applying the reverse bias voltage applying circuit 99. The time waveform 41 in FIG. 7 is restored through the process in Step S12A.

Based on the time waveform 41 restored in Step S12A, the inspection apparatus 100C specifies the position of the folding mirror 10M corresponding to the detection timing at which the electric field intensity of the terahertz wave pulse is substantially maximal. The folding mirror 10M is moved and fixed to the specified position (Step S13A). For example, in the time waveform 41 in FIG. 7, the electric field intensity is maximal (E3) at the detection timing t3. In Step S13A, the position corresponding to the detection timing t3 is determined as the position of the folding mirror 10M. Therefore, the optical path length of the probe light LP12 is set one in which the terahertz wave pulse is substantially maximal.

The electric field intensity can be detected at the timing, at which the electric field intensity of the terahertz wave pulse is maximal, by setting the position of the folding mirror 10M. Accordingly, a signal-noise ratio can be enhanced in acquiring correlation data indicating the correlation between the light intensity of the pulsed light and the electric field intensity of the terahertz wave pulse.

In the case that the Schottky barrier diode is used as the detector 132, the detector 132 detects the magnitude of the electric field intensity of the temporally-averaged terahertz wave pulse. In this case, the light intensity can quickly be set because the restoration of the terahertz wave pulse (Step S12A) and the acquisition of the maximum value (Step S13A) are skipped.

The inspection apparatus 100C determines whether the reverse bias voltage is applied (Step S14A). Whether the reverse bias voltage is applied may previously be determined, or the operator may properly input a setting value while a screen checking whether the reverse bias voltage needs to be applied is displayed on the monitor 17.

When the reverse bias voltage is applied (YES in Step S14A), the inspection apparatus 100C drives the reverse bias voltage applying circuit 99 to apply a predetermined voltage to the photovoltaic cell panel 90 (Step S15A). The inspection apparatus 100C performs the process in Step S16A. When the reverse bias voltage is not applied (NO in Step S14A), the inspection apparatus 100C skips the process in Step S15A to perform the process in Step S16A.

In the process in Step S16A, the inspection apparatus 100C acquires the correlation data indicating the correlation between the light intensity of the pulsed light and the electric field intensity of the terahertz wave pulse. Specifically, in the process in Step S16A, the light intensity of the pulsed light LP1 emitted from the femtosecond laser 121 is gradually increased from zero to necessary intensity, and the electric field intensity of the terahertz wave pulse detected in each piece of light intensity by the detector 132 is sequentially recorded. A specific example of the correlation data is described later. When acquiring the correlation data, based on the correlation data, the inspection apparatus 100C detects the light intensity when the electric field intensity is maximal (Step S17A).

The inspection apparatus 100C determines whether the reverse bias voltage applied to the photovoltaic cell panel 90 is increased (Step S18A). The determination in Step S18A is made based on whether the reverse bias voltage exceeds a specified voltage. When the applied reverse bias voltage is equal to or lower than the specified voltage (YES in Step S18A), the inspection apparatus 100C returns to Step S15A to apply the voltage, to which a necessary amount of voltage is added, to the photovoltaic cell panel 90. Then the following processes in Steps S16A and S17A are performed. When the applied reverse bias voltage exceeds the specified voltage (NO in Step S18A), the inspection apparatus 100C goes to Step S19A. Steps S14A and S18A may be omitted. In this case, the reverse bias voltage applied between the electrodes is set to a predetermined fixed value (zero, namely, including the case that the reverse bias voltage is not applied).

Figure 15:
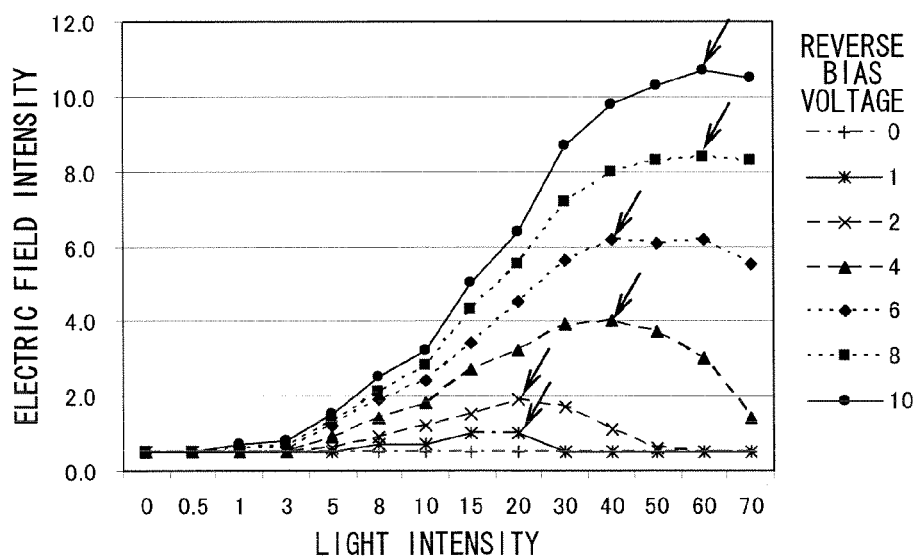
FIG. 15 is a view illustrating correlation data CD1 and a polygonal line graph of the correlation data CD1.
Figure 16:
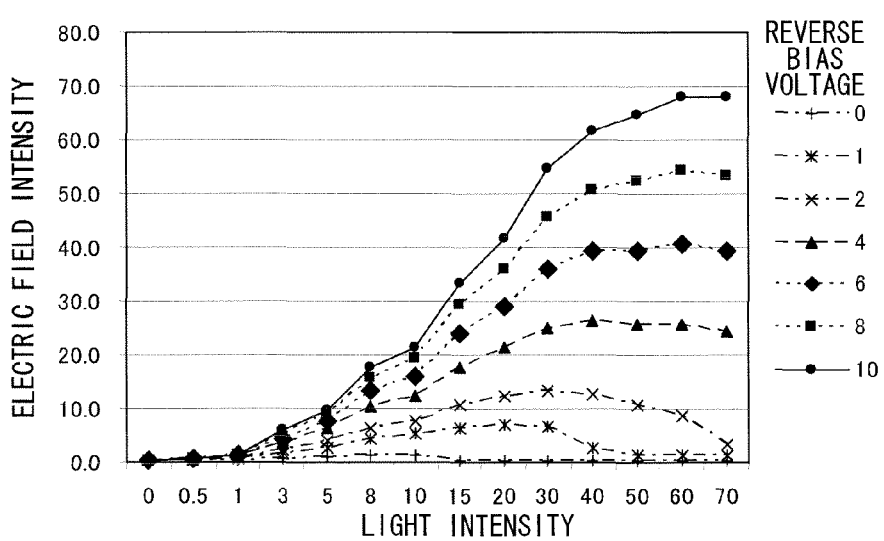
FIG. 16 is a view illustrating correlation data CD2 and a polygonal line graph of the correlation data CD2.

FIG. 15 is a view illustrating correlation data CD1 and a polygonal line graph of the correlation data CD1. FIG. 16 is a view illustrating correlation data CD2 and a polygonal line graph of the correlation data CD2. FIG. 17 is a view illustrating correlation data CD3 and a polygonal line graph of the correlation data CD3. The pieces of correlation data CD1 to CD3 are acquired by repeatedly performing the processes in Steps S14A to S18A in FIG. 14 to the positions (specifically, the positions P1 to P3 in FIG. 4) different from one another on the photovoltaic cell panel 90.

Referring to the correlation data CD1 in FIG. 15, even if the light intensity is increased from zero to 70 mW while the reverse bias voltage is zero, the detected electric field intensity is always a noise (background) level of electric field intensity (=0.5), and the correlation data CD1 is neither increased nor decreased. The magnitude of the detected electric field intensity is gradually increased with increasing reverse bias voltage from 0 V to 10 V. This is because the electric field intensity of the generated terahertz wave pulse is amplified by the reverse bias voltage.

At this point, because the generation amount of terahertz wave pulse is increased when the light intensity of the pulsed light with which the photovoltaic cell panel 90 is irradiated is increased, it is expected that the electric field intensity detected by the detector is also increased. However, as illustrated in the correlation data CD1, the electric field intensity of the terahertz wave pulse is saturated when the light intensity is increased to a certain level of magnitude, and the electric field intensity is decreased even if the light intensity is increased any more.

For example, when the light intensity is increased from 0 mW while the reverse bias voltage is set to 1 V, the electric field intensity is gradually increased, and the electric field intensity is maximal at the light intensity of 15 mW or 20 mW. That is, 15 mW or 20 mW becomes the peak light intensity. However, when the light intensity is further increased from 20 mW to 30 mW, the electric field intensity is decreased. Similarly, when the reverse bias voltage is set to 2 V or 4 V, the electric field intensity is maximal at the light intensity of 20 mW or 40 mW, respectively, and then the electric field intensity is decreased.

The phenomenon, in which the electric field intensity is not proportional to the magnitude of the light intensity but is saturated, is attributed to the following fact. That is, the photoexcited carrier is generated when the photo device such as the photovoltaic cell panel 90 is irradiated with the pulsed light emitted from the femtosecond laser 121. The generated photoexcited carrier is influenced by the reverse bias voltage, the internal electric field, the diffusion, and the like, and attracted by the collector electrode (such as the light receiving surface electrode 96). In the case that the pulsed light has the relatively small light intensity, the photoexcited carrier is sufficiently attracted to the electrode. On the other hand, when the light intensity is increased, the photoexcited carrier is insufficiently attracted. As a result, the portion irradiated with the pulsed light is filled with the photoexcited carrier. Therefore, because the amount of photoexcited carrier newly generated by the irradiation of the pulsed light is decreased, it is considered that the electric field intensity of the terahertz wave pulse is also decreased. Accordingly, it is expected that the following equation (1) holds when the electric field intensity is maximal.

(generation amount of photoexcited carrier)=(amount of photoexcited carrier absorbed by reverse bias, internal electric field, or diffusion) (1)

In the pieces of correlation data CD1 to CD3 in FIGS. 15 to 17, the change in light intensity and application of the bias voltage are performed under the substantially same condition. However, the magnitude of the detected electric field intensity varies in each piece of data. More particularly, the electric field intensity in the correlation data CD2 in FIG. 16 is wholly larger than that in the pieces of correlation data CD1 and CD3. The electric field intensity is decreased in order of the correlation data CD3 and the correlation data CD1.

It is considered that the difference in electric field intensity among the pieces of correlation data CD1 to CD3 is caused by observation points of the pieces of correlation data CD1 to CD3 and a difference in distance from the light receiving surface electrode 96. The intensity of external electric field increases and the acceleration of the photoexcited carrier becomes high as is located closer to the light receiving surface electrode 96. As a result, the intensity of the terahertz wave is considered to be increased. That is, as illustrated in FIG. 4, it is considered that, because the positions P2, P3, and P1 are sequentially distanced from light receiving surface electrode 96, the pieces of detected electric field intensity are decreased in this order.

Referring to FIG. 14, based on the correlation data, the inspection apparatus 100C sets the light intensity for inspection (Step S19A). Specifically, the light intensity setting part 27 sets the light intensity (peak light intensity) at the maximum electric field intensity to the light intensity for inspection. For example, as is clear from the pieces of correlation data CD1 to CD3 in FIGS. 15 to 17, when the photo device is irradiated with the pulsed light having the excessively strong light intensity, the electric field intensity of the terahertz wave pulse generated from the photo device is decreased in reverse. A boundary at which the electric field intensity starts to decrease is specified from the correlation data, which allows the electric field intensity of the terahertz wave pulse detected by the detector 132 to be maximized without uselessly increasing the light intensity. Therefore, the long service life and the reduction of maintenance cost of the femtosecond laser 121 can be achieved while the signal-noise ratio is improved.

As illustrated in the pieces of correlation data CD1 to CD3, sometimes the peak light intensity varies depending on the magnitude of the reverse bias voltage applied to the photovoltaic cell panel 90. In Step S19A, a reverse bias voltage having specific magnitude is properly selected from reverse bias voltages having some pieces of magnitude, the peak light intensity that is determined at the selected reverse bias voltage is set to the light intensity for inspection. The reverse bias voltage may be selected by an arbitrary standard. For example, it is conceivable that the light intensity at which the electric field intensity recorded in the correlation data exceeds a predetermined threshold is selected as the peak light intensity.

In Step S19A, the light intensity for measurement is set in conjunction with the peak light intensity. Alternatively, the light intensity for measurement may be set to another piece of light intensity. In consideration of the long lifetime of the femtosecond laser 121, desirably the light intensity of the pulsed light for measurement is set so as not to exceed the peak light intensity. However, the light intensity that slightly exceeds the peak light intensity is allowable.

Then, in the inspection apparatus 100C, the photovoltaic cell panel 90 is inspected such that the pulsed light having the light intensity set in Step S19A is emitted from the femtosecond laser 121 (Step S20A). In Step S20A, various points of the photovoltaic cell panel 90 is irradiated with the pulsed light (pump light LP11), and the electric field intensity of the generated terahertz wave pulse is detected by the detector 132.

In Step S20A, substantially same inspection as the inspection (1) (the inspection based on the time waveform of the terahertz wave pulse, see FIG. 6) or the inspection (2) (the inspection based on the electric field intensity distribution of the terahertz wave pulse, see FIG. 9) is performed.

Figure 18:
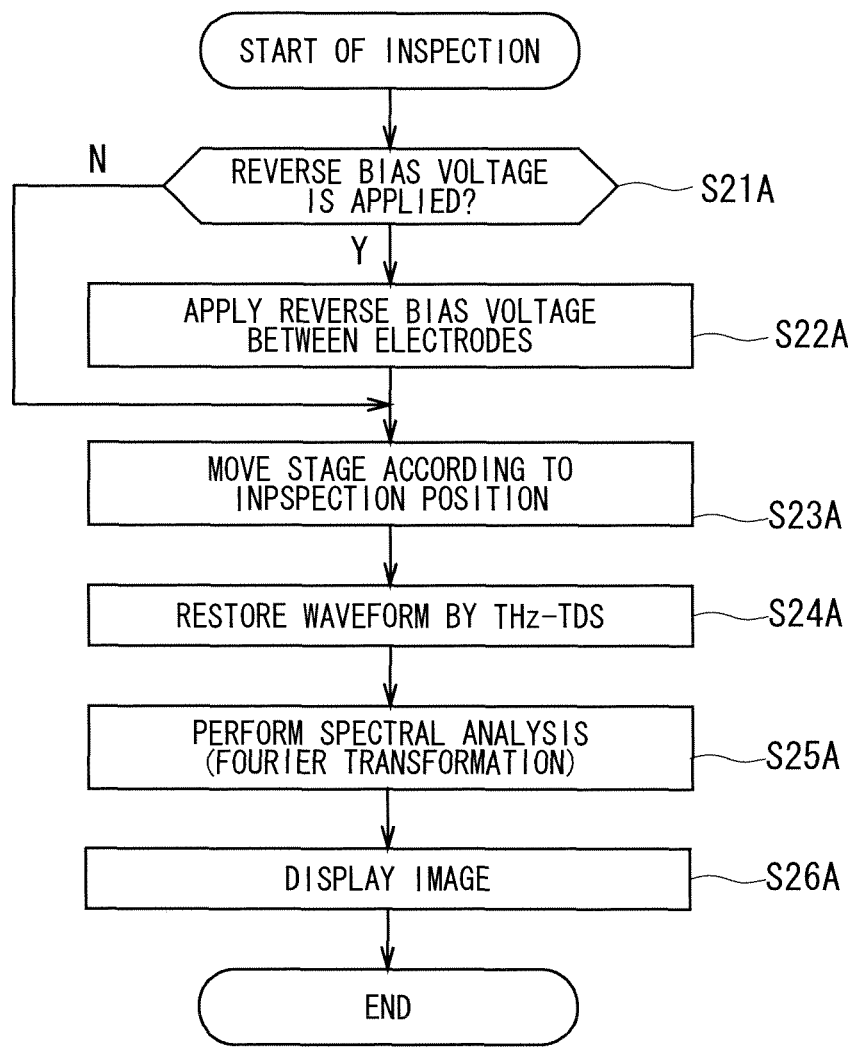
FIG. 18 is a flowchart of the inspection (1) of the fourth preferred embodiment.

FIG. 18 is a flowchart of the inspection (1) of the fourth preferred embodiment. When the inspection (1) is started, the inspection apparatus 100C determines whether the reverse bias voltage is applied (Step S21A). When the reverse bias voltage is applied (YES in Step S21A), the voltage having the same magnitude as the reverse bias voltage at which the light intensity is set in Step S19A is applied between the electrodes of the photovoltaic cell panel 90 (Step S22A).

For example, in the correlation data CD1, the peak light intensity is 20 mW when the reverse bias voltage is set to 2 V as illustrated in FIG. 15. Therefore, when the light intensity is set to 20 mW in Step S19A, the reverse bias voltage of 2 V is applied in Step S22A. When the reverse bias voltage is not applied (NO in Step S21A), the inspection apparatus 100C skips the process in Step S22A to perform the process in Step S23A.

In Step S23A, the inspection apparatus 100C moves the photovoltaic cell panel 90 according to the inspection position. Using the manipulation inputting part 18, the operator previously assigns the inspection position as the data (coordinate data) relating to the position on the photovoltaic cell panel 90 to be inspected. In order to irradiate the inspection position with the pulsed light, the control part 16 drives the motor 15 to move the stage 11 based on the coordinate data. The operator may move the stage 11 to move the photovoltaic cell panel 90 according to the inspection position.

When the movement of the photovoltaic cell panel 90 is completed, the inspection apparatus 100C restores the time waveform of the terahertz wave pulse generated by the irradiation of the pump light LP11 by the THz-TDS (Step S24A). Specifically, the process in Step S24A is identical to that in Step S12A in FIG. 6. However, the photovoltaic cell panel 90 is irradiated with the pulsed light having the light intensity set in Step S19A in FIG. 14. Similarly to the time waveform 41 in FIG. 7, the time waveform of the terahertz wave pulse generated in the inspection position is restored by performing the process in Step S24A.

Therefore, the characteristic of the depletion layer of the pn junction 97 can be inspected in the inspection position by restoring the time waveform. For example, the shape failure of the depletion layer can be detected by inspecting the existence or non-existence of the detection of the terahertz wave pulse or by comparing an amplitude of the electric field intensity of the constructed time waveform to the standard data. The shape failures of various photoexcited carrier generation areas of the photovoltaic cell can be detected through the same processing.

The inspection apparatus 100C performs the spectral analysis based on the restored time waveform (Step S25A). In the process in Step S25A, the spectrum analyzer 23 performs the Fourier transformation to the time waveform, thereby acquiring the spectral distribution with respect to the terahertz wave pulse as illustrated in FIG. 8.

The characteristic of the depletion layer of the pn junction 97 formed in the inspection position can be inspected from the spectral distribution acquired in Step S25A. For example, the mixing of the impurity in the inspection position can be estimated when the spectral intensity at a specific frequency is significantly lower than the reference value in the spectral distribution. The kind or the concentration of the impurity can be estimated from the absorbed frequency or the spectral intensity. The spectral analysis in Step S25A may be omitted.

When the spectral analysis in Step S25A is completed, the inspection apparatus 100C displays the image indicating the inspection result on the monitor 17 (Step S26A). Specifically, for example, the time waveform of the terahertz wave pulse acquired in Step S24A and the spectral distribution (see FIG. 12) acquired in Step S25A are displayed as the analysis result on the monitor 17. The inspection (1) is described above. The inspection (2) of the fourth preferred embodiment will be described below.

<Inspection (2)>

Figure 19:
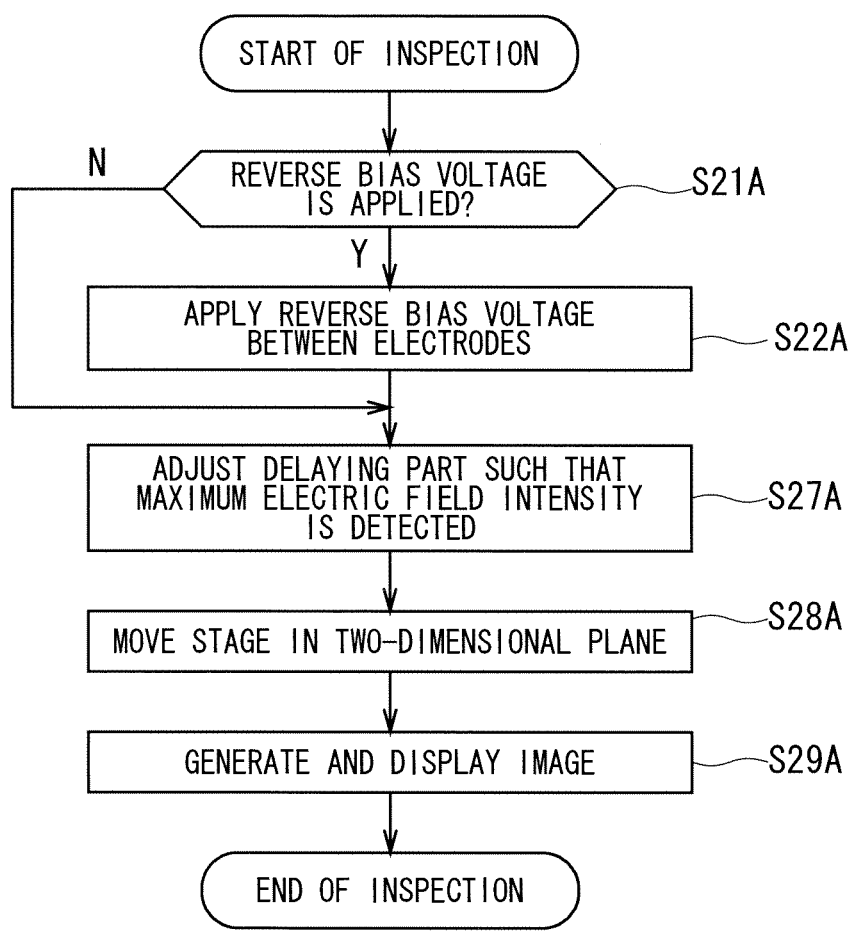
FIG. 19 is a flowchart of the inspection (2) of the fourth preferred embodiment.

FIG. 19 is a flowchart of the inspection (2) of the fourth preferred embodiment. In the inspection (1), the spectral analysis of the time waveform of the terahertz wave pulse generated by the irradiation of the pump light LP11 are performed to the specific area on the photovoltaic cell panel 90. On the other hand, in the inspection (2), the state of the photoexcited carrier generation area is inspected with respect to the whole surface of the photovoltaic cell panel 90.

When the inspection (2) is started, the inspection apparatus 100C determines whether the reverse bias voltage is applied to the photovoltaic cell panel 90 (Step S21A). When the reverse bias voltage is applied to the photovoltaic cell panel 90 (YES in Step S21A), the reverse bias voltage is applied between the electrodes (Step S22A). The flow in the inspection (2) is identical to that of the processes in Steps S21A and S22A in the inspection (1).

The inspection apparatus 100C adjusts the delaying part 131 such that the electric field intensity of the terahertz wave pulse detected by the detector 132 is maximal (Step S27A). In the process in Step S27A, the folding mirror 10M is disposed in the position that is determined in Step S13A in FIG. 14. Thus, the maximum value of the electric field intensity of the terahertz wave pulse is detected to facilitate the detection of the terahertz wave pulse. Alternatively, the electric field intensity of the terahertz wave pulse may be detected at another piece of detection timing by disposing the folding mirror 10M in another position.

The inspection apparatus 100 drives the motor 15 to move the photovoltaic cell panel 90 in the two-dimensional plane (Step S28Aa). Specifically, after the photovoltaic cell panel 90 is moved in one direction along the main scanning direction, the photovoltaic cell panel 90 is moved in the sub-scanning direction orthogonal to the main scanning direction by a necessary distance, and moved in the other direction along the main scanning direction again. The movement of the photovoltaic cell panel 90 is repeatedly performed as needed basis. The photovoltaic cell panel 90 is irradiated with the pulsed light having the light intensity set in Step S19A in FIG. 14 in association with the movement of the photovoltaic cell panel 90, and the electric field intensity of the terahertz wave pulse generated by the irradiation of the pulsed light is detected by the detector 132. Therefore, the electric field intensity distribution is acquired in the photovoltaic cell panel 90.

When acquiring the electric field intensity of the terahertz wave pulse, the inspection apparatus 100C generates the image indicating the electric field intensity distribution, and displays the image on the monitor 17 (Step S29A). Specifically, the electric field intensity distribution image I1 is displayed on the monitor 17 as illustrated in FIG. 10.

As illustrated in FIG. 10, in the photovoltaic cell panel 90, the electric field intensity is maximal around the light receiving surface electrode 96, and the electric field intensity is decreased with distance from the light receiving surface electrode 96. The formation status of the photoexcited carrier generation area can be recognized at once with respect to the inspection target area of the photovoltaic cell panel 90 by generating and displaying the electric field intensity distribution image I1. The crystal defect of the polycrystalline silicon and the like can also be estimated from the abnormality of the detected electric field intensity.

The configurations of the inspection apparatuses 100A and 100B in FIGS. 11 and 12 can be adopted as the configurations of the irradiation part 12 and the detecting part 13 of the inspection apparatus 100C.

5. Modification

The preferred embodiments are described above. However, the present invention is not limited to the preferred embodiments, but various modifications can be made.

For example, in the preferred embodiments, the photovoltaic cell panel 90 is inspected using the pulsed light having the wavelength near 800 nm. Alternatively, the substrate in which the photovoltaic cell panel 90 or another photo device is formed may be inspected using pulsed light having a second harmonic wave of 1.5 µm and 1.0 µm. For example, the photo device formed in a wafer may be inspected.

The light intensity may be measured in the femtosecond laser 121, or the pulsed light may be measured after emitted from the femtosecond laser 121. As to the pulsed light measuring method, part of the pulsed light is extracted to measure the light intensity and the remaining light intensity may be calculated, or the pulsed light may be measured while the whole pulsed light is interrupted.

In acquiring the correlation data, the light intensity of the pulsed light (pump light LP11) with which the photovoltaic cell panel 90 is irradiated may be changed while the pulsed light emitted from the femtosecond laser 121 is kept constant. Alternatively, the light intensity of the pulsed light LP1 emitted from the femtosecond laser 121 may be changed.

The configurations of the preferred embodiments and the modifications may be combined when being consistent with each other.

While the invention has been shown and described in detail, the foregoing description is in all aspects illustrative and not restrictive. It is therefore understood that numerous modifications and variations can be devised without departing from the scope of the invention.

What is claimed is:

1. An inspection apparatus that inspects a photo device, said inspection apparatus comprising:
an irradiation part that irradiates said photo device with pulsed light; and a detecting part that detects an electromagnetic wave pulse, which is generated by said photo device according to said pulsed light irradiation, wherein said detecting part includes:

a detector that detects electric field intensity of said electromagnetic wave pulse according to irradiation of probe light emitted from a light source of said pulsed light; and a delaying part that delays detection timing at which said detector detects said electromagnetic wave pulse by changing a temporal difference between a time said electromagnetic wave pulse reaches said detector and a time said probe light reaches said detecting part, the inspection apparatus further comprising a time waveform constructing part that constructs a time waveform from electromagnetic wave intensity of an electromagnetic pulse detected by the detector at said plurality of pieces of detection timing.

2. The inspection apparatus according to claim 1, further comprising a control part that controls said delaying part to obtain said detection timing at which electric field intensity of said electromagnetic wave pulse is maximal.

3. The inspection apparatus according to claim 1, further comprising a spectrum analyzing part that performs a spectral analysis by performing a Fourier transformation based on said time waveform of said electromagnetic wave pulse, said time waveform being constructed by said time waveform constructing part.

4. The inspection apparatus according to claim 1, further comprising a relatively-moving mechanism that moves said photo device relative to said irradiation part in a two-dimensional plane.

5. The inspection apparatus according to claim 1, wherein an optical axis of said pulsed light is obliquely incident to a light receiving surface from a light receiving surface side of said photo device.

6. The inspection apparatus according to claim 1, wherein an optical axis of said pulsed light is perpendicularly incident to a light receiving surface from a light receiving surface side of said photo device.

7. The inspection apparatus according to claim 6, wherein said detecting part detects an electromagnetic wave pulse emitted onto said light receiving surface side.

8. The inspection apparatus according to claim 1, wherein said electromagnetic wave pulse generated in said photo device includes a terahertz wave having a frequency range of 0.01 terahertz to 10 terahertz.

9. The inspection apparatus according to claim 1, wherein said irradiation part includes a femtosecond laser that emits a pulsed light, and said inspection apparatus further includes:

a control part that controls said irradiation part to change light intensity of said pulsed light; and a light intensity setting part that sets said light intensity of said pulsed light emitted from said femtosecond laser based on peak light intensity of said pulsed light when said light intensity is changed by said control part, said peak light intensity being obtained when said electric field intensity of said electromagnetic wave is maximal.

10. An inspection method for inspecting a photo device, the inspection method comprising the steps of:

(a) irradiating said photo device with pulsed light; and (b) detecting an electromagnetic wave pulse, which is generated by said photo device according to said pulsed light irradiation, wherein said (a) step is the step of irradiating a light receiving surface of a photo device with said pulsed light while changing light intensity of pulsed light emitted from a femtosecond laser, and said inspection method further includes the steps of:

(c) acquiring peak light intensity of said pulsed light when said electric field intensity of said electromagnetic wave detected in said (b) step is maximal; and (d) detecting said electric field intensity of said electromagnetic wave pulse, generated by said photo device, with a detector by irradiating said photo device with pulsed light having light intensity, which is defined based on said peak light intensity acquired in said (c) step.

11. The inspection method according to claim 10, wherein said (d) step is the step of irradiating said photo device with pulsed light having light intensity that does not exceed said peak light intensity.

12. The inspection method according to claim 10, further comprising the step of (e) applying a reverse bias voltage to said photo device when said (b) step is performed.

13. The inspection method according to claim 10, wherein said (b) step includes the steps of:

(b-1) branching said pulsed light from said femtosecond laser into pump light oriented toward said photo device and probe light oriented toward said detector; and (b-2) changing an optical path length of one of a first optical path of said pump light and a second optical path of said probe light.

14. The inspection method according to claim 13, wherein said (b) step includes the step of (b-3) acquiring peak optical path length when said electric field intensity detected by said detector is maximal when said optical path length of one of said first optical path and said second optical path is changed in said (b-2) step, and said (a) step is the step of changing light intensity of said pulsed light while said optical path length of one of said first optical path and said second optical path is fixed to said peak optical path length.

15. The inspection method according to claim 10, wherein said detector in said (b) step is constructed by a Schottky barrier diode.

16. An inspection apparatus that inspects a photo device, said inspection apparatus comprising:

an irradiation part that irradiates said photo device with pulsed light;

a detecting part that detects an electromagnetic wave pulse, which is generated by said photo device according to said pulsed light irradiation; and a reverse bias applying circuit that applies a reverse bias voltage to a photo device formed in said photo device.

17. An inspection apparatus that inspects a photo device, said inspection apparatus comprising:

an irradiation part that irradiates said photo device with pulsed light; and a detecting part that detects an electromagnetic wave pulse, which is generated by said photo device according to said pulsed light irradiation, wherein said photo device is a crystalline silicon photovoltaic cell, and a wavelength of said pulsed light is equal to or lower than 1 micrometer.

* * * * *